US012029499B2

(12) United States Patent
St. Pierre et al.

(10) Patent No.: US 12,029,499 B2
(45) Date of Patent: Jul. 9, 2024

(54) BIOPSY NEEDLE VISUALIZATION

(71) Applicant: HOLOGIC, INC., Marlborough, MA (US)

(72) Inventors: Shawn St. Pierre, Marlborough, MA (US); Stephen Grantz, Marlborough, MA (US); Thomas Fisk, Marlborough, MA (US); Mark Guetersloh, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 525 days.

(21) Appl. No.: 17/041,087

(22) PCT Filed: May 3, 2019

(86) PCT No.: PCT/US2019/030615
§ 371 (c)(1),
(2) Date: Sep. 24, 2020

(87) PCT Pub. No.: WO2019/213532
PCT Pub. Date: Nov. 7, 2019

(65) Prior Publication Data
US 2021/0100626 A1    Apr. 8, 2021

Related U.S. Application Data

(60) Provisional application No. 62/666,869, filed on May 4, 2018.

(51) Int. Cl.
A61B 34/20    (2016.01)
A61B 8/00    (2006.01)
(Continued)

(52) U.S. Cl.
CPC ............ *A61B 34/20* (2016.02); *A61B 8/0841* (2013.01); *A61B 8/4488* (2013.01); *A61B 8/463* (2013.01);
(Continued)

(58) Field of Classification Search
None
See application file for complete search history.

(56) References Cited

U.S. PATENT DOCUMENTS

| | | |
|---|---|---|
| 4,821,727 A | 4/1989 | Levene et al. |
| 4,907,156 A | 6/1990 | Doi et al. |

(Continued)

FOREIGN PATENT DOCUMENTS

| | | |
|---|---|---|
| CN | 202161328 | 3/2012 |
| CN | 102429678 | 5/2012 |

(Continued)

OTHER PUBLICATIONS

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

(Continued)

*Primary Examiner* — Jason M Ip
*Assistant Examiner* — Renee C Langhals
(74) *Attorney, Agent, or Firm* — Merchant & Gould P.C.

(57) ABSTRACT

Methods and systems providing guidance for operation of a biopsy needle based on ultrasonic imaging. Ultrasonic waves are emitted and detected by a ultrasonic transducer to generate image data. A biopsy needle is identified within the generated image data, and the biopsy needle may be in a pre-fire configuration. Based on the identification of the biopsy needle, the methods and systems may determine a predicted location of the biopsy needle based at least in part on biopsy needle properties. The predicted location of the biopsy needle may be the predicated location of the biopsy needle in its post-fire configuration. At least one indicator may be displayed indicating the determined predicted location.

15 Claims, 10 Drawing Sheets

(51) Int. Cl.

| | | |
|---|---|---|
| *A61B 8/08* | (2006.01) | |
| *A61B 10/02* | (2006.01) | |
| *A61B 17/34* | (2006.01) | |
| *A61B 34/00* | (2016.01) | |
| *A61B 90/00* | (2016.01) | |
| *G01S 7/52* | (2006.01) | |
| *G01S 15/89* | (2006.01) | |
| *G06N 20/00* | (2019.01) | |
| *G16H 10/40* | (2018.01) | |
| *G16H 20/40* | (2018.01) | |
| *G16H 30/40* | (2018.01) | |
| *G16H 40/63* | (2018.01) | |

(52) U.S. Cl.
CPC ............ *A61B 8/485* (2013.01); *A61B 8/5215* (2013.01); *A61B 10/0275* (2013.01); *A61B 17/3403* (2013.01); *A61B 34/25* (2016.02); *A61B 90/39* (2016.02); *G01S 7/52073* (2013.01); *G01S 15/8906* (2013.01); *G06N 20/00* (2019.01); *G16H 10/40* (2018.01); *G16H 20/40* (2018.01); *G16H 30/40* (2018.01); *G16H 40/63* (2018.01); *A61B 8/0825* (2013.01); *A61B 8/481* (2013.01); *A61B 2017/3413* (2013.01); *A61B 2034/2063* (2016.02); *A61B 2034/2065* (2016.02); *A61B 2090/378* (2016.02); *A61B 2090/3925* (2016.02); *A61B 2090/3983* (2016.02)

(56) References Cited

U.S. PATENT DOCUMENTS

| | | |
|---|---|---|
| 5,078,142 A | 1/1992 | Siczek et al. |
| 5,129,911 A | 7/1992 | Siczek et al. |
| 5,133,020 A | 7/1992 | Giger et al. |
| 5,219,351 A | 6/1993 | Teubner |
| 5,240,011 A | 8/1993 | Assa |
| 5,280,427 A | 1/1994 | Magnusson |
| 5,289,520 A | 2/1994 | Pellegrino et al. |
| 5,343,390 A | 8/1994 | Doi et al. |
| 5,386,447 A | 1/1995 | Siczek |
| 5,415,169 A | 5/1995 | Siczek et al. |
| 5,426,685 A | 6/1995 | Pellegrino et al. |
| 5,491,627 A | 2/1996 | Zhang et al. |
| 5,594,769 A | 1/1997 | Pellegrino et al. |
| 5,609,152 A | 3/1997 | Pellegrino et al. |
| 5,735,264 A | 4/1998 | Siczek et al. |
| 5,769,086 A | 6/1998 | Ritchart et al. |
| 5,773,832 A | 6/1998 | Sayed et al. |
| 5,803,912 A | 9/1998 | Siczek et al. |
| 6,022,325 A | 2/2000 | Siczek et al. |
| 6,101,236 A | 8/2000 | Wang et al. |
| 6,102,866 A | 8/2000 | Nields et al. |
| 6,245,028 B1 | 6/2001 | Furst et al. |
| 6,293,282 B1 | 9/2001 | Lemelson |
| 6,459,925 B1 | 10/2002 | Nields et al. |
| 6,468,226 B1 | 10/2002 | McIntyre, IV |
| 6,480,565 B1 | 11/2002 | Ning |
| 6,620,111 B2 | 9/2003 | Stephens et al. |
| 6,626,849 B2 | 9/2003 | Huitema et al. |
| 6,638,235 B2 | 10/2003 | Miller et al. |
| 6,683,934 B1 | 1/2004 | Zhao |
| 6,733,458 B1 | 5/2004 | Steins |
| 6,758,824 B1 | 7/2004 | Miller et al. |
| 6,987,331 B2 | 1/2006 | Koeppe |
| 7,123,684 B2 | 10/2006 | Jing et al. |
| 7,245,694 B2 | 7/2007 | Jing et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,697,660 B2 | 4/2010 | Ning |
| 7,702,142 B2 | 4/2010 | Ren et al. |
| 7,760,924 B2 | 7/2010 | Ruth et al. |
| 7,787,936 B2 | 8/2010 | Kressy |
| 7,831,296 B2 | 11/2010 | DeFreitas et al. |
| 7,869,563 B2 | 1/2011 | DeFreitas |
| 7,991,106 B2 | 8/2011 | Ren et al. |
| 8,532,745 B2 | 9/2013 | DeFreitas et al. |
| 8,594,274 B2 | 11/2013 | Hoernig et al. |
| 9,020,579 B2 | 4/2015 | Smith |
| 9,901,309 B2 | 2/2018 | DeFreitas et al. |
| 10,092,358 B2 | 10/2018 | DeFreitas |
| 10,335,094 B2 | 7/2019 | DeFreitas |
| 10,357,211 B2 | 7/2019 | Smith |
| 10,456,213 B2 | 10/2019 | DeFreitas |
| 10,595,954 B2 | 3/2020 | DeFreitas |
| 2001/0038681 A1 | 11/2001 | Stanton et al. |
| 2002/0113681 A1 | 8/2002 | Byram |
| 2003/0018272 A1 | 1/2003 | Treado et al. |
| 2003/0073895 A1 | 4/2003 | Nields et al. |
| 2003/0135115 A1 | 7/2003 | Burdette et al. |
| 2004/0077938 A1 | 4/2004 | Mark et al. |
| 2004/0081273 A1 | 4/2004 | Ning |
| 2004/0127789 A1 | 7/2004 | Ogawa |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0084060 A1 | 4/2005 | Seppi et al. |
| 2005/0089205 A1 | 4/2005 | Kapur |
| 2005/0111718 A1 | 5/2005 | MacMahon |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2006/0009693 A1 | 1/2006 | Hanover et al. |
| 2006/0025680 A1 | 2/2006 | Jeune-Iomme |
| 2006/0030784 A1 | 2/2006 | Miller et al. |
| 2006/0098855 A1 | 5/2006 | Gkanatsios et al. |
| 2006/0129062 A1 | 6/2006 | Nicoson et al. |
| 2006/0155209 A1 | 6/2006 | Miller et al. |
| 2006/0149194 A1 | 7/2006 | Conston |
| 2006/0257009 A1 | 11/2006 | Wang |
| 2006/0269040 A1 | 11/2006 | Mertelmeier |
| 2007/0016067 A1 | 1/2007 | Webster |
| 2007/0019846 A1 | 1/2007 | Bullitt et al. |
| 2007/0114424 A1 | 5/2007 | Danielsson et al. |
| 2007/0225600 A1 | 9/2007 | Weibrecht et al. |
| 2007/0263765 A1 | 11/2007 | Wu |
| 2008/0019581 A1 | 1/2008 | Gkanatsios et al. |
| 2008/0045833 A1 | 2/2008 | DeFreitas et al. |
| 2008/0101537 A1 | 5/2008 | Sendai |
| 2008/0152086 A1 | 6/2008 | Hall |
| 2008/0187095 A1 | 8/2008 | Boone et al. |
| 2008/0198966 A1 | 8/2008 | Hjarn |
| 2009/0003519 A1 | 1/2009 | DeFreitas |
| 2009/0080604 A1 | 3/2009 | Shores et al. |
| 2009/0143674 A1 | 6/2009 | Nields |
| 2009/0171244 A1 | 7/2009 | Ning |
| 2009/0296882 A1 | 12/2009 | Gkanatsios et al. |
| 2010/0034348 A1 | 2/2010 | Yu |
| 2010/0098214 A1 | 4/2010 | Star-Lack et al. |
| 2010/0135558 A1 | 6/2010 | Ruth et al. |
| 2010/0152570 A1 | 6/2010 | Navab |
| 2010/0208037 A1 | 8/2010 | Sendai |
| 2010/0305439 A1 | 12/2010 | Shai |
| 2011/0019891 A1 | 1/2011 | Puong |
| 2011/0069808 A1 | 3/2011 | Defreitas et al. |
| 2011/0087132 A1 | 4/2011 | DeFreitas et al. |
| 2011/0110576 A1 | 5/2011 | Kreeger |
| 2011/0112549 A1* | 5/2011 | Neubach .............. A61B 34/20 606/130 |
| 2011/0182402 A1 | 7/2011 | Partain |
| 2011/0237927 A1 | 9/2011 | Brooks et al. |
| 2011/0237947 A1* | 9/2011 | Boctor .................. A61B 8/485 600/443 |
| 2011/0245659 A1* | 10/2011 | Ma ........................ A61B 5/066 600/424 |
| 2011/0313288 A1 | 12/2011 | Chi Sing |
| 2012/0014504 A1 | 1/2012 | Jang |
| 2012/0134464 A1 | 5/2012 | Hoernig et al. |
| 2012/0238870 A1 | 9/2012 | Smith et al. |

(56) References Cited

U.S. PATENT DOCUMENTS

| | | |
|---|---|---|
| 2012/0239087 A1 | 9/2012 | Field |
| 2013/0022165 A1 | 1/2013 | Jang |
| 2013/0044861 A1 | 2/2013 | Muller |
| 2013/0108138 A1 | 5/2013 | Nakayama |
| 2013/0259193 A1 | 10/2013 | Packard |
| 2014/0064444 A1 | 3/2014 | Oh |
| 2014/0073913 A1 | 3/2014 | DeFreitas et al. |
| 2014/0094695 A1* | 4/2014 | Jain ............... A61B 8/481 600/424 |
| 2016/0000399 A1* | 1/2016 | Halmann ....... A61B 17/3403 600/461 |
| 2016/0022364 A1 | 1/2016 | DeFreitas et al. |
| 2016/0235380 A1 | 8/2016 | Smith |
| 2016/0324501 A1 | 11/2016 | Vignon |
| 2017/0340352 A1* | 11/2017 | Stone ............ A61B 17/3421 |
| 2018/0000446 A1* | 1/2018 | Lu .................. A61B 8/587 |
| 2018/0132927 A1 | 5/2018 | Chen |
| 2018/0132944 A1* | 5/2018 | Yan ................... G06T 7/74 |
| 2018/0256118 A1 | 9/2018 | DeFreitas |
| 2019/0008605 A1 | 1/2019 | Matsushima et al. |
| 2019/0015173 A1 | 1/2019 | DeFreitas |
| 2019/0105017 A1 | 4/2019 | Hastings |
| 2019/0110924 A1 | 4/2019 | Moreno |
| 2019/0290221 A1 | 9/2019 | Smith |
| 2020/0000442 A1 | 1/2020 | Vancamberg |
| 2020/0046303 A1 | 2/2020 | DeFreitas |
| 2020/0093562 A1 | 3/2020 | DeFreitas |
| 2020/0205928 A1 | 7/2020 | DeFreitas |
| 2020/0281662 A1 | 9/2020 | Cong |
| 2020/0390404 A1 | 12/2020 | DeFreitas |
| 2021/0000553 A1 | 1/2021 | St. Pierre |

FOREIGN PATENT DOCUMENTS

| | | |
|---|---|---|
| CN | 106687049 | 5/2017 |
| CN | 107106126 A | 8/2017 |
| CN | 107666876 A | 2/2018 |
| DE | 102011087127 | 5/2013 |
| EP | 2236085 | 6/2010 |
| EP | 2491863 | 8/2012 |
| EP | 1986548 | 1/2013 |
| EP | 2656789 | 10/2013 |
| EP | 3060132 | 4/2019 |
| JP | 2000-107178 | 4/2000 |
| JP | 2003-531516 | 10/2003 |
| JP | 2006-519634 | 8/2006 |
| JP | 2007-130487 | 5/2007 |
| JP | 2009-522005 | 6/2009 |
| JP | 2009-526618 | 7/2009 |
| JP | 2010-137004 | 6/2010 |
| JP | 2012/501750 | 1/2012 |
| JP | 2014-507250 | 3/2014 |
| JP | 2015-506794 | 3/2015 |
| WO | 93/17620 | 9/1993 |
| WO | 94/06352 | 3/1994 |
| WO | 1997/00649 | 1/1997 |
| WO | 00/51484 | 9/2000 |
| WO | 2005/110230 | 11/2005 |
| WO | 2005/112767 | 12/2005 |
| WO | 2006/055830 | 5/2006 |
| WO | 2006/058160 | 6/2006 |
| WO | 08/014670 | 2/2008 |
| WO | 2008/054436 | 5/2008 |
| WO | 2010/028208 | 3/2010 |
| WO | 2012/068373 | 5/2012 |
| WO | 2012/112627 | 8/2012 |
| WO | 2012/122399 | 9/2012 |
| WO | 2013/078476 | 5/2013 |
| WO | 2013/123091 | 8/2013 |
| WO | 2015/061582 | 4/2015 |
| WO | 2016/103094 A1 | 6/2016 |
| WO | 2016/184746 A1 | 11/2016 |
| WO | 2019/213532 | 11/2019 |

OTHER PUBLICATIONS

Dromain, Clarisse et al., "Dual-energy contrast-enhanced digital mammography: initial clinical results", European Radiology, Sep. 14, 2010, vol. 21, pp. 565-574.

Reynolds, April, "Stereotactic Breast Biopsy: A Review", Radiologic Technology, vol. 80, No. 5, Jun. 1, 2009, pp. 447M-464M, XP055790574.

International Search Report and Written Opinion of the International Searching Authority for International Patent Application No. PCT/US2019/030615 dated Sep. 17, 2019, 13 pages.

"SuperSonic to feature Aixplorer Ultimate at ECR", AuntiMinnie. com, 3 pages (Feb. 2018).

European Extended Search Report in Application 21198835.7, dated Feb. 17, 2022, 8 pages.

Xia, et al., "Looking Beyond the Imaging Plane: 3D Needle Tracking with a Linear Array Ultrasound Probe", Sci Rep 7, 3674 (2017), https:doi.org/10.1038/s41598-017-03886-4, 9 pages.

"Filtered Back Projection", (NYGREN), published May 8, 2007, URL: http://web.archive.org/web/19991010131715/http://www.owlnet.rice.edu/~elec539/Projects97/cult/node2.html, 2 pgs.

Berg WA et al., "Combined screening with ultrasound and mammography vs mammography alone in women at elevated risk of breast cancer", JAMA 299:2151-2163, 2008.

Canadian Office Action in Application 2829349, dated Oct. 15, 2018, 4 pages.

Carton AK, et al., "Dual-energy contrast-enhanced digital breast tomosynthesis—a feasibility study", BR J Radiol. Apr. 2010;83 (988):344-50.

Chen SC, et al., "Initial clinical experience with contrast-enhanced digital breast tomosynthesis", Acad Radio. Feb. 2007 14(2):229-38.

Chinese 2nd Office Action in Application 201480058064.5, dated Jul. 16, 2019, 5 pgs.

Diekmann F., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain C., et al., "Contrast-enhanced digital mammography", Eur J Radiol. 2009; 69:34-42.

European Communication in Application 10707751.3, dated Oct. 4, 2018, 5 pages.

European Communication in Application 10707751.3, dated Aug. 7, 2019, 6 pages.

European Extended Search Report dated Jul. 18, 2014 in EP App 12754521.8, 7 pages.

European Extended Search Report for European Patent Application No. 14770362.3 dated Sep. 28, 2016, 8 pgs.

European Extended Search Report in Application 14855181.5, dated May 15, 2017, 7 pages.

European extended Search Report in Application 18153706.9, dated Jun. 1, 2018, 8 pages.

European Mar. 23, 2009 European Search Report in connection with counterpart European Application No. 07750818.

European Office Action in Application 10707751.3, dated Feb. 19, 2018, 5 pgs.

Freiherr G., "Breast tomosynthesis trials show promise", Diagnostic Imaging—San Francisco 2005, V27; N4:42-48.

Giger, M. et al., "An "Intelligent" Workstation for Computer-aided Diagnosis", RadioGraphics, (1993), 13(3): 647-656.

Giger, M. et al., "Development of a "smart" workstation for use in mammography", Proceedings of SPIE, (1991), 45: 101-103.

Hologic, "Lorad StereoLoc II" Operator's Manual 9-500-0261, Rev. 005, 2004, 78 pgs.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

(56) References Cited

OTHER PUBLICATIONS

ICRP Publication 60: 1990 Recommendations of the International Commission on Radiological Protection, 12 pages.
Japanese Notice of Final Rejection in Application 2016-526115, dated Jun. 24, 2019, 5 pages.
Jochelson M., et al., "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Kopans, et.al. Will tomosynthesis replace conventional mammography? Plenary Session SFN08: RSNA 2005.
Lehman CD, et al. MRI evaluation of the contralateral breast in women with recently diagnosed breast cancer. N Engl J Med 2007; 356:1295-1303.
Lewin JM, et al., Dual-energy contrast-enhanced digital subtraction mammography: feasibility. Radiology 2003; 229:261-268.
Lindfors KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Observations by Third Party, Remarks concerning European patent application No. 10707751.3 according to Article 115 EPC, dated Apr. 24, 2014, 8 pgs.
PCT Feb. 20, 2008 International Search Report and Written Opinion in connection with corresponding International patent application No. PCT/US2007/04006, 7 pgs.
PCT International Preliminary Report on Patentability in International Application PCT/US2014/061994, dated Apr. 26, 2016, 5 pages.
PCT International Search Report and Written Opinion in Application PCT/US2010/025873, dated Aug. 2, 2010, 19 pgs.
PCT International Search Report in Application PCT/US2014/026164, dated Jul. 28, 2014, 1 page.
PCT International Written Report for International Application PCT/US2014/026164, dated Jul. 28, 2014, 12 pgs.
PCT Written Opinion in International Application PCT/US2014/061994, dated Jan. 22, 2015, 4 pages.
PCT/US12/28334 International Search Report and Written Opinion, dated Jul. 5, 2012, 7 pages.
Poplack SP, et al., Digital breast tomosynthesis: initial experience in 98 women with abnormal digital screening mammography. AJR Am J Roentgenology Sep. 2007 189(3):616-23.
Prionas ND, et al., Contrast-enhanced dedicated breast CT: initial clinical experience. Radiology. Sep. 2010 256(3):714-723.
Rafferty E. et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., Full field breast tomosynthesis. Radiol Manage. Sep.-Oct. 2005; 27(5):25-31.
Weidner N, Semple JP, Welch WR, Folkman J. Tumor angiogenesis and metastasis: correlation in invasive breast carcinoma. New England Journal of Medicine 1991; 324:1-8.
Weidner N, The importance of tumor angiogenesis: the evidence continues to grow. AM J Clin Pathol. Nov. 2004 122(5):696-703.
"SuperSonic to feature Aixplorer Ultimate at ECR"; obtained online on Dec. 21, 2023 at: https://www.auntminnie.com/clinical-news/ultrasound/article/15619739/supersonic-to-feature-aixplorer-ultimate-at-ecr, published Feb. 25, 2018, 3 pages.
"SuperSonic Imagine holds 30 international patent families protecting its unique ultrasound imaging technology around the world", obtained online on Dec. 21, 2023 at: https://www.supersonicimagine.com/Aixplorer-MACH2/TECHNOLOGY, 1 page.
Carriere, Jay et al., "Real-time needle shape prediction in soft-tissue based on image segmentation and particle filtering", 2016 IEEE International Conference on Advanced Intelligent Mechatronics (AIM), Banff, AB, Canada, 2016, 6 pages.

* cited by examiner

BIOPSY NEEDLE VISUALIZATION

CROSS-REFERENCE TO RELATED APPLICATIONS

This application is a National Stage Application of PCT/US2019/030615, filed May 3, 2019, which claims priority to and the benefit of U.S. Provisional Patent Application Ser. No. 62/666,869, filed May 4, 2018, entitled "Biopsy Needle Visualization," the disclosures of which are hereby incorporated by reference herein in their entireties. To the extent appropriate, a claim of priority is made to each of the above disclosed applications.

BACKGROUND

A biopsy is a procedure that is used to extract tissue from a targeted location of a patient for further examination. For example, a lesion or mass may be identified within the patient, and a sample of that lesion or mass is desired for further testing, analysis, or examination. During some biopsy procedures, such as a percutaneous core biopsy, a surgeon or medical professional inserts a biopsy needle into the patient through an incision of the skin of the patient. To target and/or visualize the lesion accurately with the biopsy needle, various imaging modalities are employed, including the use of ultrasound technology to view an image of the needle in a subcutaneous position. While such use of ultrasound technology is useful, prior ultrasound guided biopsy technology provides visual indication but limited additional information about the lesion or of the biopsy needle and provides little guidance or insights to the medical professional performing the biopsy procedure. The biopsy procedure thus relied heavily on the skill, experience, and intuition of the medical professional.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for the localization of an implanted marker through ultrasound technology along with additional combinations of other modalities.

In an aspect, the technology relates to a method for providing guidance for operation of a biopsy needle. The method includes emitting an array of ultrasonic sound waves from an ultrasonic transducer of an ultrasound probe, detecting reflected ultrasonic sound waves by the ultrasonic transducer, wherein the reflected ultrasonic sound waves include at least a portion of the array of ultrasonic sound waves after being reflected from an interior of a patient, and generating image data from the reflected ultrasonic sound waves. The method also includes identifying, by a processor, within the generated image data, at least a portion of a biopsy needle within the interior of the patient. The method further includes based at least in part on the identification of the biopsy needle, determining, by a processor, a predicted location of an aspect of the biopsy needle based at least in part on one or more biopsy needle properties stored in memory operatively connected to the processor. In addition, the method includes displaying, on a display operatively connected to the processor, an ultrasound image based on the generated image data; and displaying, on the ultrasound image, at least one indicator for the aspect of the predicted location of the biopsy needle.

In an example, identifying the biopsy needle includes identifying the biopsy needle in a pre-fire configuration, and the predicted location of the biopsy needle is a predicted location of the biopsy needle in a post-fire configuration. In another example, displaying the at least one indicator for the predicted location of the biopsy needle includes displaying at least one of a tip indicator indicating a predicted biopsy needle tip location or an aperture indicator indicating a predicted biopsy needle aperture location. In yet another example, identifying the biopsy needle comprises receiving a user input identifying the biopsy needle in the ultrasound image. In still another example, identifying the biopsy needle comprises analyzing, by the processor, the generated image data by image analysis techniques to identify the biopsy needle. In still yet another example, the method further includes determining a deflection probability for a needle tip location based on at least one of: (1) experimental data for the type of biopsy needle and (2) one or more stored properties of the biopsy needle, the properties including at least one of a needle length, a needle gauge, a needle wall thickness, a needle material composition, a needle tip geometry, a throw length, and a needle firing mechanism property.

In another example, the one or more stored properties of the biopsy needle are based on user input regarding a type of the biopsy needle. In yet another example, the input regarding the type of the biopsy needle includes a model and manufacturer of the biopsy needle. In still another example, the method also includes determining the deflection probability is further based on tissue properties of the interior of the patient along a fire trajectory for the biopsy needle. In still yet another example, the tissue properties are based on an input identifying the tissue properties.

In another example, the method also includes determining the tissue properties by: determining, by the processor, a fire trajectory for the biopsy needle based on the generated image data; receiving elastography data for tissue along at least a portion of the fire trajectory for the biopsy needle; and determining the tissue properties based on the received elastography data. In yet another example, the method further includes displaying a deflection probability indicator on the ultrasound image, wherein the deflection probability indicator indicates a range for a post-fire tip location based on the determined deflection probability. In still another example, the deflection probability indicator is one of an ellipse, rectangle, square, triangle, or a circle. In still yet another example, the deflection probability indicator indicates a range of probabilities for the post-fire tip location.

In another example, the deflection probability indicator comprises a heatmap. In yet another example, the method also includes determining that the predicted location is outside of the ultrasound image; and in response to determining that the predicted location is outside of the ultrasound image, displaying an alert. In still another example, the method also includes determining a maximum pre-fire biopsy needle depth for which a predicted post-fire biopsy needle tip location remains within the ultrasound image; and displaying a maximum needle depth indicator, wherein the maximum needle depth indicator indicates the determined maximum pre-fire biopsy needle depth. In still yet another example, the maximum needle depth indicator is a line segment perpendicular to a fire trajectory of the biopsy needle.

In another example, the method further includes determining that the biopsy needle has diverted out of an imaging plane of the ultrasound image; and in response to determining that the biopsy needle has diverted out of the imaging plane for the ultrasound image, performing at least one of the following operations: displaying an alert indicating that the biopsy needle has diverted out of the imaging plane for the ultrasound image; or altering a beamform emitted from the ultrasound probe to compensate for the biopsy needle diversion out of the imaging plane. In yet another example, determining that the biopsy needle has diverted out of the imaging plane for the ultrasound image further includes: determining a first apparent depth for the biopsy needle at a first time; determining a second apparent depth for the biopsy needle at a second time subsequent to the first time, the second apparent depth being greater than the first apparent depth; determining a third apparent depth for the biopsy needle at a third time subsequent to the second time, the third apparent depth being less than the second apparent depth; and based on the third apparent depth being less than the second apparent depth and the second apparent depth being greater than the first apparent depth, determining that the biopsy needle has diverted out of the imaging plane for the ultrasound image.

In another example, a tip indicator is a graphical element having a shape based on a geometry of a tip of the biopsy needle. In still another example, the aperture indicator includes two line segments perpendicular to a fire trajectory of the biopsy needle. In yet another example, the tip indicator and aperture indicator are displayed concurrently.

In an aspect, the technology relates to a system including an ultrasound probe comprising an ultrasonic transducer, the ultrasonic transducer configured to emit an array of ultrasonic sound waves and detect reflected ultrasonic sound waves, wherein the reflected ultrasonic sound waves include at least a portion of the array of ultrasonic sound waves after being reflected within an interior of a patient; a display; at least one processor operatively connected to the display and the ultrasound probe; and memory, operatively connected to the at least one processor, storing instructions that when executed by the at least one processor perform a set of operations. The set of operations includes generating image data from the reflected ultrasonic sound waves; identifying, by the processor, within the generated image data, a biopsy needle within the interior of the patient; based at least in part on the identification of the biopsy needle, determining, by the processor, a predicted location of an aspect of the biopsy needle based on one or more stored properties of the biopsy needle; displaying, on a display operatively connected to the processor, an ultrasound image based on the generated image data; and displaying, on the ultrasound image, at least one indicator for the predicted location of the aspect of the biopsy needle.

In an aspect, the technology relates to a method for providing guidance for operation of a biopsy needle. The method includes displaying a user interface for selecting a type of biopsy needle to be used for a biopsy procedure; receiving as input in the user interface, the input indicating the type of biopsy needle to be used for the biopsy procedure; based on the input indicating the type of biopsy needle, determining needle properties for the biopsy needle, wherein the needle properties include at least one of a needle length, a needle gauge, a needle wall thickness, a needle material composition, a needle tip geometry, and a needle firing mechanism property; based on the determined needle properties, determining a deflection probability for a post-fire tip location of the biopsy needle; emitting an array of ultrasonic sound waves from an ultrasonic transducer of an ultrasound probe; detecting reflected ultrasonic sound waves by the ultrasonic transducer, wherein the reflected ultrasonic sound waves include at least a portion of the array of ultrasonic sound waves after being reflected from an interior of a patient; generating an ultrasound image from the reflected ultrasonic sound waves; identifying the biopsy needle within generated ultrasound image; and based on the identification of the biopsy needle and the determined deflection probability for the post-fire tip location of the biopsy needle, displaying a deflection probability indicator on the ultrasound image, wherein the deflection probability indicator indicates a range for a predicted post-fire tip location based on the determined deflection probability.

In an example, the input in the user interface indicates a make and model of the biopsy needle. In another example, determining needle properties for the biopsy needle include querying a database containing the needle properties based on the input received from the user interface. In yet another example, the method of claim 25, wherein the deflection probability indicator is one of an ellipse, a circle, a square, a rectangle, or a triangle. In still another example, the deflection probability indicator indicates a range of probabilities for the post-fire tip location. In still yet another example, the deflection probability indicator comprises a heatmap indicating a range of probabilities for the post-fire tip location.

In another example, determining the deflection probability is further based on tissue properties of the interior of the patient along a fire trajectory for the biopsy needle. In still another example, the tissue properties are based on user input identifying the tissue properties. In yet another example, the method further includes determining the tissue properties by: determining a fire trajectory for the biopsy needle based on the generated ultrasound image; receiving elastography data for tissue along at least a portion of the fire trajectory for the biopsy needle; and determining the tissue properties based on the received elastography data. In still yet another example, determining the deflection probability is based on a mathematical analysis for determining flex of a needle having the determined needle properties. In another example, the method includes aggregating ultrasound image data for a plurality of insertions of biopsy needles into a patient; training a machine learning tool based on the aggregated ultrasound image data; and wherein determining the deflection probability is determined at least in part using the trained machine learning tool.

In an aspect, the system relates to an ultrasound probe comprising an ultrasonic transducer, the ultrasonic transducer configured to emit an array of ultrasonic sound waves and detect reflected ultrasonic sound waves, wherein the reflected ultrasonic sound waves include at least a portion of the array of ultrasonic sound waves after being reflected within an interior of a patient; a display; at least one processor operatively connected to the display and the ultrasound probe; and memory, operatively connected to the at least one processor, storing instructions that when executed by the at least one processor perform a set of operations. The set of operations include displaying a user interface on the display for selecting a type of biopsy needle to be used for a biopsy procedure; receiving as input in the user interface, the input indicating the type of biopsy needle to be used for the biopsy procedure; based on the input indicating the type of biopsy needle, determining needle properties for the biopsy needle, wherein the needle properties include at least one of a needle length, a needle gauge, a needle wall thickness, a needle material composition, a needle tip geometry, and a needle firing mechanism property; based on the determined needle properties, determining a deflection probability for a post-fire tip location of the biopsy needle; generating an ultrasound image from the reflected ultrasonic sound waves; identifying the biopsy needle within generated ultrasound image; and based on the identification of the biopsy needle and the determined deflection probability for the post-fire tip location of the biopsy needle, displaying a deflection probability indicator on the ultrasound image, wherein the deflection probability indicator indicates a range for a predicted post-fire tip location based on the determined deflection probability.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1A:
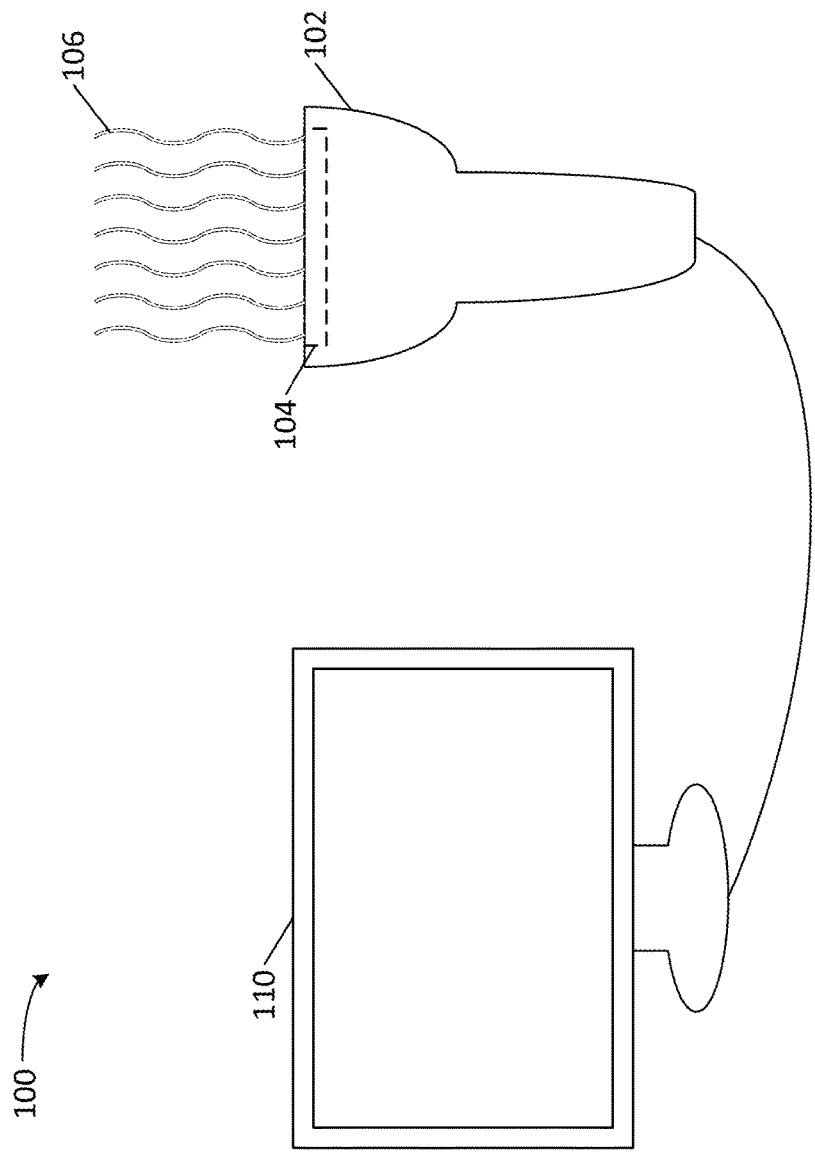
FIG. 1A depicts an example of a biopsy needle visualization system.

Proper positioning of a biopsy needle is important for a successful biopsy procedure. In situations where the biopsy needle is not properly positioned, a biopsy procedure may need to be performed repeatedly until a desired sample is obtained. Incorrect positioning can also lead to repeated steps during the procedure, additional sample being acquired during the same procedure, and/or a patient having to return for additional follow-up biopsy procedures. Proper positioning of a biopsy needle, however, becomes more difficult with the use of different biopsy needles. As an example, some biopsy needles are spring-loaded and have other "firing" mechanisms that cause a portion of the biopsy needle to extend to capture a sample. For instance, an outer cannula of a biopsy needle may be inserted into the patient, and upon a release mechanism being triggered, an inner cannula with an aperture is fired from within the outer cannula such that the inner cannula extends further into the patient to capture a sample. Examples of such biopsy needles include the Celero® biopsy device and the Sertera® biopsy device from Hologic, Inc., of Marlborough, Massachusetts. Even with ultrasound images of such biopsy needles in their subcutaneous position, the post-fire positions of the biopsy needle are still unknown. That is, while a portion of a biopsy needle in its pre-fire configuration may be seen on an ultrasound image, the final location of the biopsy needle in its post-fire configuration is not necessarily discernable from an ultrasound image alone.

Many biopsy procedures, even those with prior ultrasound technology, relied heavily on the skill, experience, and intuition of the medical professional performing the biopsy procedure. While some well-trained and experienced medical professionals are able to approximate where the biopsy needle might be located in its post-fire position, less experienced medical professionals may have trouble making such approximations. Further, the biopsy needles vary between different brands and models, adding further unpredictability to the process. For instance, one biopsy needle may deflect more than another when fired, and such deflection may also depend on the particular tissue for which the biopsy needle will pass through when fired. These deflections are extremely difficult, if not impossible, for even experienced surgeons to predict. In addition, there is variability in the nature and composition of the patient's breast tissue, can cause some unpredictability in the final location of the biopsy needle, post-fire.

To alleviate those problems, among others, the present technology provides for a biopsy needle visualization system that provides more precise and useful feedback during the biopsy procedure to allow a medical professional to more accurately position the biopsy needle. As example, the biopsy needle visualization system may provide indicia for a predicted location and/or position of the biopsy needle in its post-fire configuration based on its pre-fire configuration. The predicted location of the biopsy needle may be displayed as an overlay preferably on a live, or real-time, ultrasound image of the biopsy needle and the targeted location for the biopsy needle. Thus, the medical professional is provided with additional guidance to perform a more accurate sampling of tissue using the biopsy needle. For instance, if the surgeon sees that the predicted location is not the targeted location, the medical professional is able to adjust the biopsy needle to the proper position. The predicted location of the biopsy needle may be displayed as a set of biopsy prediction indicators that may indicate the predicted location of the tip of the biopsy needle and the aperture of the biopsy needle. The predictions also may be based on the properties of the biopsy needle that is currently being used to perform the biopsy. Accordingly, the guidance provided to the surgeon is specific to the specific biopsy needle in use, allowing for the medical professional to perform the biopsy even if he or she has never used that particular needle before. The composition of the patient's breast tissue which may be determined or indicated by the medical professional during the procedure may also be used to determine the predicted location of the biopsy needle, providing for an even more accurate prediction. Thus, the technologies described herein provide improved performance for both well-experienced and less-experienced surgeons.

FIG. 1A depicts an example of a biopsy needle visualization system 100. The biopsy needle visualization system 100 includes an ultrasound probe 102 that includes an ultrasonic transducer 104. The ultrasonic transducer 104 is configured to emit an array of ultrasonic sound waves 106. The ultrasonic transducer 104 converts an electrical signal into ultrasonic sound waves 106. The ultrasonic transducer 104 may also be configured to detect ultrasonic sound waves, such as ultrasonic sound waves that have been reflected from internal portions of a patient. In some examples, the ultrasonic transducer 104 may incorporate a capacitive transducer and/or a piezoelectric transducer, as well as other suitable transducing technology.

The ultrasonic transducer 104 is also operatively connected (e.g., wired or wirelessly) to a display 110. The display 110 may be a part of a computing system, including processors and memory configured to produce and analyze ultrasound images. Further discussion of a suitable computing system is provided below with reference to FIG. 1G. The display 110 is configured to display ultrasound images based on an ultrasound imaging of a patient. The ultrasound imaging performed in the biopsy needle visualization system 100 is primarily B-mode imaging, which results in a two-dimensional ultrasound image of a cross-section of a portion of the interior of a patient. The brightness of the pixels in the resultant image generally corresponds to amplitude or strength of the reflected ultrasound waves. Other ultrasound imaging modes may also be utilized. While the term transceiver is used herein, the term is intended to cover both transmitters, receivers, and transceivers, along with any combination thereof.

Figure 1B:
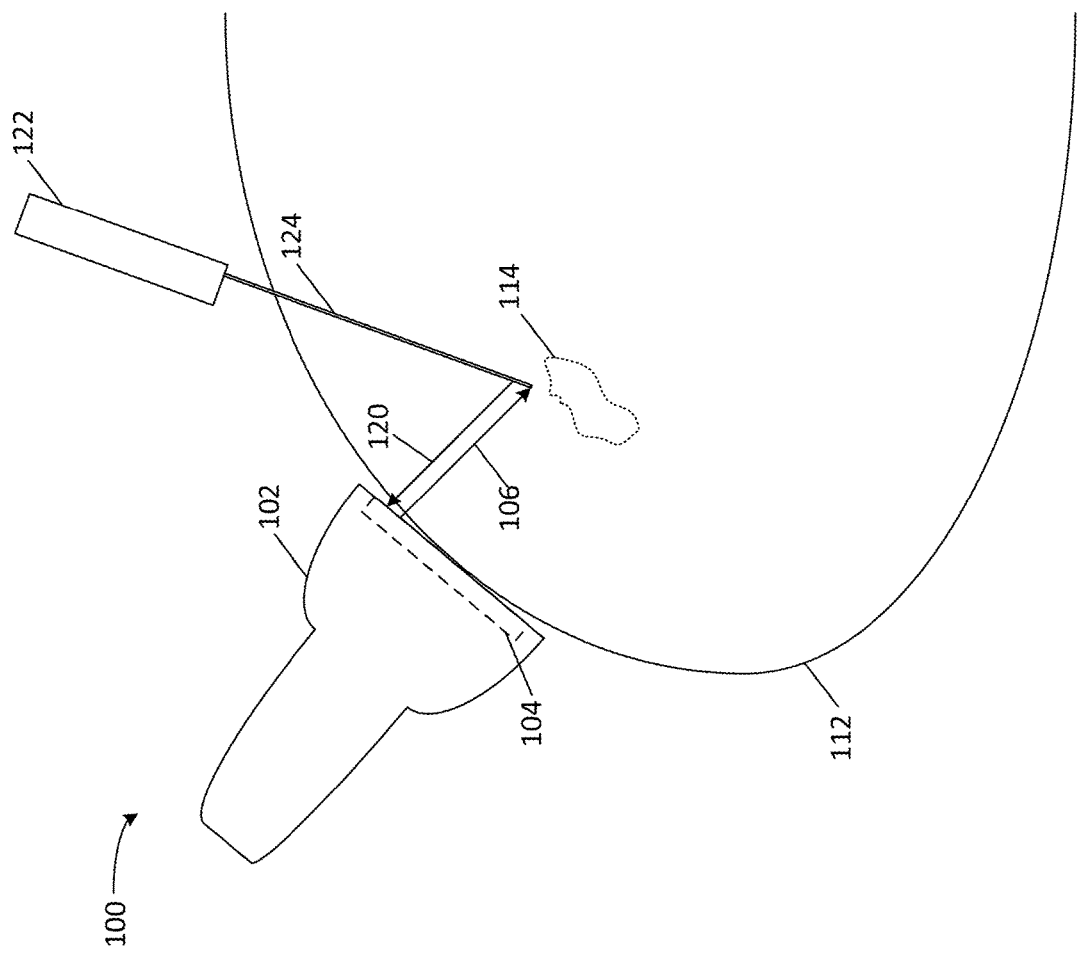
FIG. 1B depicts an example of the biopsy needle visualization system with a biopsy needle in a pre-fire configuration.

FIG. 1B depicts an example of the biopsy needle visualization system 100 with a biopsy needle 124 in a pre-fire configuration. The ultrasound probe 102 is in contact with a portion of the patient 112, such as a breast of the patient 112. In the position depicted in FIG. 1B, the ultrasound probe 102 is being used to image a portion of the patient 112 containing a lesion 114. A biopsy device 122 having a biopsy needle 124 is inserted into the patient 112. The biopsy needle 124 is depicted in its pre-fire configuration. To image the portion of the patient 112 containing the biopsy needle 124, the ultrasonic transducer 104 emits an array of ultrasonic sound waves 106 into the interior of the patient 112. A portion of the ultrasonic sound waves 106 are reflected off internal features of the patient 112 as well as the biopsy needle 124, when the biopsy needle 124 is in the field of view, and return to the ultrasound probe 102 as reflected ultrasonic sound waves 120. The reflected ultrasonic sound waves 120 may be detected by the ultrasonic transducer 104. For instance, the ultrasonic transducer 104 receives the reflected ultrasonic sound waves 120 and converts the ultrasonic sound waves 120 into an electric signal that can be processed and analyzed to generate ultrasound image data on display 110.

Figure 1C:
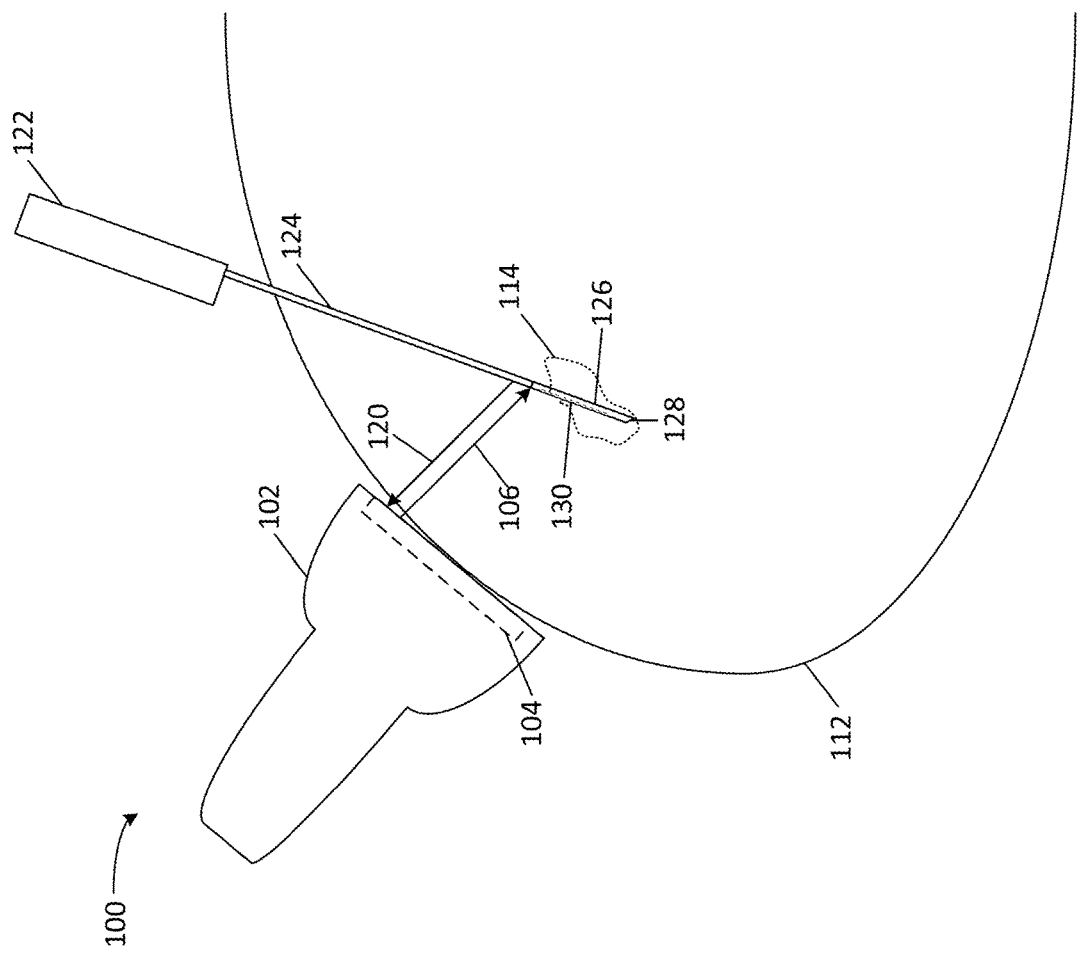
FIG. 1C depicts an example of the biopsy needle visualization system with the biopsy needle in a post-fire configuration.

FIG. 1C depicts an example of the biopsy needle visualization system 100 with the biopsy needle 124 in a post-fire configuration. The biopsy needle visualization system 100 as depicted in FIG. 1C is substantially the same as the biopsy needle visualization system 100 depicted in FIG. 1B, with the exception that the biopsy needle 124 is in a post-fire configuration. In the post-fire configuration, the biopsy needle has a throw portion 126 that has extended from the biopsy needle 124. In some examples, the throw portion 126 may be an inner cannula of the biopsy needle 124. The throw portion 126 also includes an aperture 130 for collecting tissue from the lesion 114. The aperture 130 is located between a biopsy needle tip 128 and the portion of the biopsy needle 124 from the pre-fire configuration of the biopsy needle 124.

As can be seen from FIGS. 1B-1C, the biopsy needle 124 is inserted into the patient in a direction towards the lesion 114. When the biopsy needle 124 in its pre-fire configuration reaches a particular point within the patient 112, the biopsy needle 124 is fired. The firing of the biopsy needle 124 is often triggered by pressing or otherwise manipulating a trigger located on the biopsy device 122. When the biopsy needle 124 is fired, the throw portion 126 extends from the biopsy needle 124. In the example depicted, it is desired that the aperture 130 of the throw portion 126 be located at the lesion 114 such that tissue sample from the lesion 114 may be collected. As discussed above, determining the proper location and positioning of the biopsy needle 124 in the pre-firing configuration to achieve the desired aperture 130 and tip 128 location in a post-firing configuration is both important and difficult. By generating ultrasound imagery during the biopsy procedure that includes the biopsy needle 124, analysis may be performed on the image to provide additional guidance as to the positioning of the needle, as discussed further below with reference to FIGS. 2-4.

Figure 1D:
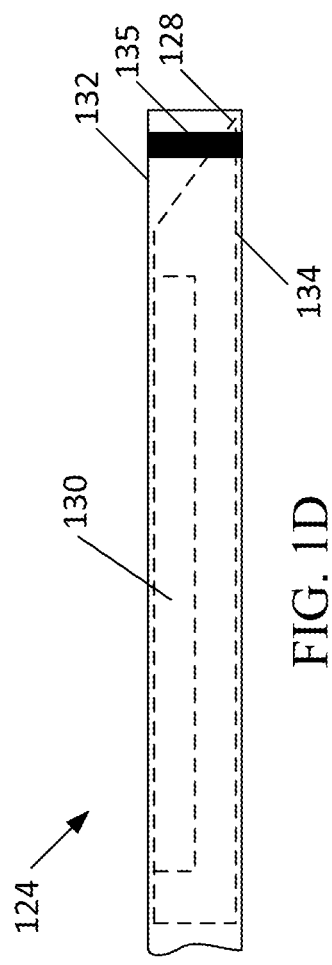
FIG. 1D depicts an example a biopsy needle in a pre-fire configuration.
Figure 1E:
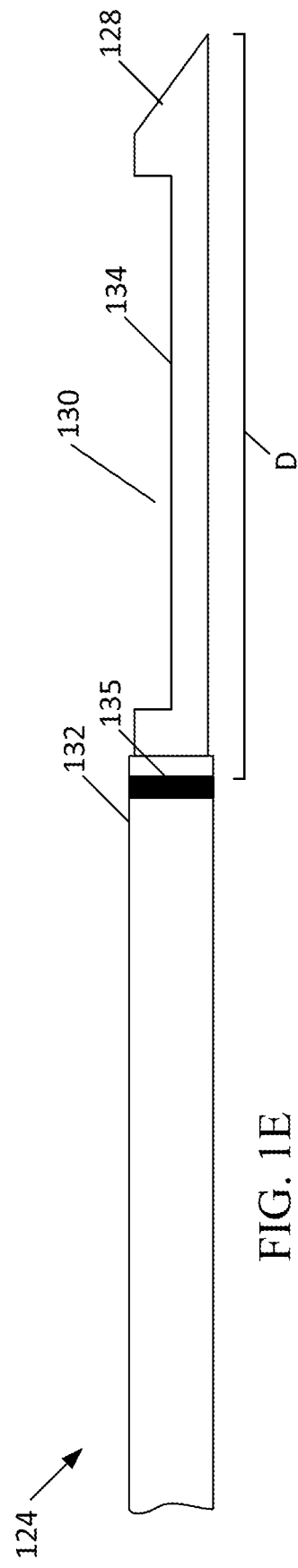
FIG. 1E depicts an example of the biopsy needle of FIG. 1D during a firing process.
Figure 1F:
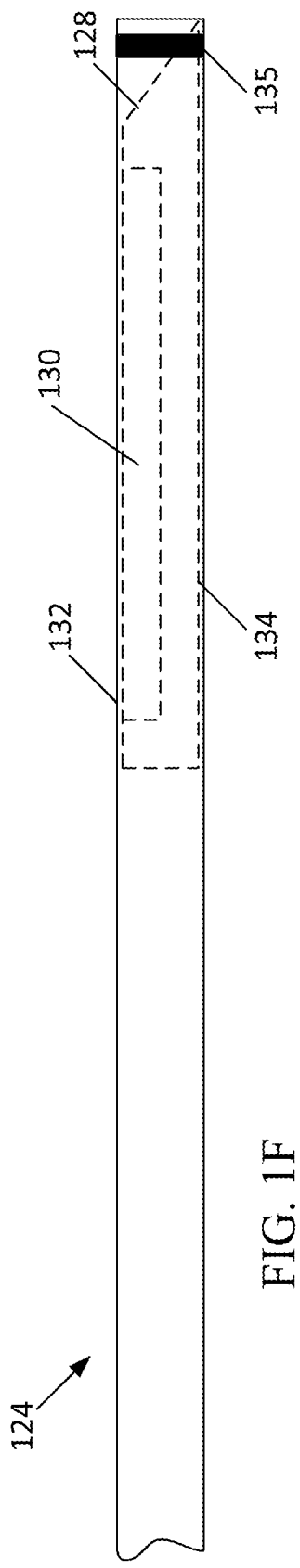
FIG. 1F depicts an example of the biopsy needle of FIGS. 1D-1E in a post-fire configuration.

FIGS. 1D-1F depict an example of biopsy needle 124 at multiple stages during the firing process and are discussed concurrently. In particular, FIG. 1D depicts the biopsy needle 124 in a pre-fire configuration, FIG. 1E depicts the biopsy needle 124 during the firing process, and FIG. 1F depicts the biopsy needle 124 in the post-fire configuration. The example biopsy needle 124 includes an outer cannula 132 and an inner cannula 134. The inner cannula 134 includes an aperture 130 and a biopsy needle tip 128. During the firing process, the inner cannula 134 advances from the outer cannula 132. The distance the inner cannula 134 extends from the outer cannula 132 may be referred to as the throw distance. Once the inner cannula 134 has extended from the outer cannula 132 (as depicted in FIG. 1E), tissue is captured in the aperture 130. In some examples, a vacuum mechanism may be attached to the biopsy needle 124 to pull tissue into the aperture 130. With the tissue captured in the aperture 130, the outer cannula 132 is advanced over the inner cannula 134 (as shown in FIG. 1F), which cuts the tissue thereby separating the tissue captured in the aperture 130 from remaining tissue of the patient. Both the outer cannula 132 (alone) or the outer cannula 132 and the inner cannula 134 may be manufactured, in whole or in part, from a material that displays a high degree of echogenicity, which causes those elements to appear brighter in a resulting ultrasound image. The biopsy needle 124 is then in a complete post-fire configuration and may be retracted from the patient 112. The tissue captured in the aperture 130 may then be removed from the biopsy needle 124 for further analysis and examination. The procedure described above may be performed a number of times to remove multiple biopsy samples. At the end of the biopsy procedure a marker marking the location of the biopsied site may be inserted into the biopsy location.

Another case, only a portion 135 of the outer cannula 132 is formed from a high-echogenicity material, which may completely or partially surround the circumference of the inner cannula. The portion 135 at a location on the outer cannula 132 that is a known distance D from the tip 128 of the inner cannula 134 when at its maximum extent. This distance D may be specific to a particular needle type or manufacturer, for example. Here, the known distance D locates the portion 135 distal from the tip 128, and opposite the aperture 130 therefrom, but other locations are contemplated. By forming only the portion 135 of the outer cannula 132 of a high echogenic material and a known distance D from the tip 128, accuracy of the post-fire location of the inner cannula 134 may be improved. More specifically, if a biopsy needle having an outer cannula formed completely from a high echogenic material is utilized, it may be unknown to the processor analyzing the image (or the surgeon performing the procedure) if the apparent tip of the outer cannula identified is the actual tip of that component. Given the depth of penetration of the ultrasound waves, it is possible that the apparent tip of the outer cannula may simply be a portion of the outer cannula located at the maximum depth of that wave penetration. In the configuration depicted in FIGS. 1D-1E, however, once the portion 135 is detected, the location of the actual tip 128 may be more easily determined.

Figure 1G:
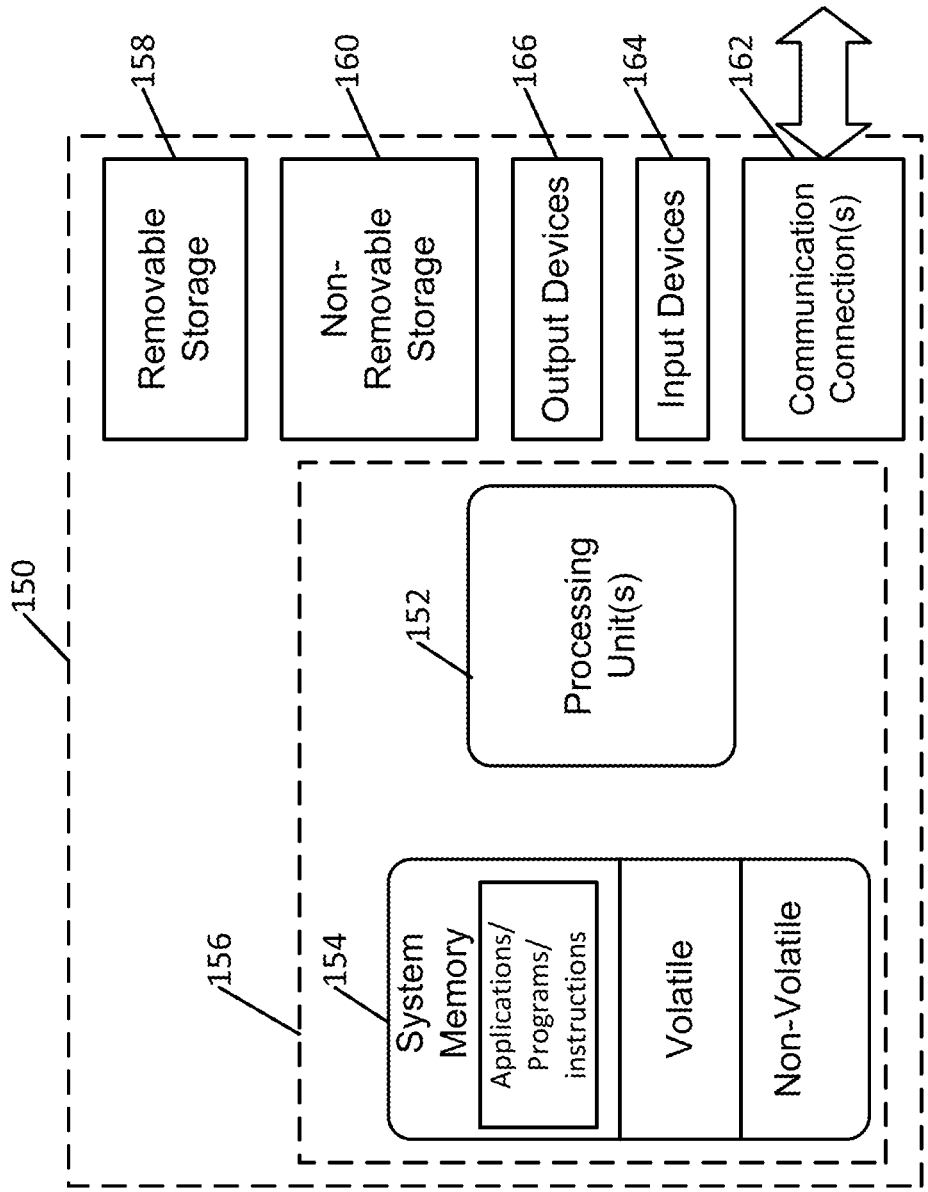
FIG. 1G depicts an example of a suitable operating environment for incorporation into the biopsy needle visualization system.

FIG. 1G depicts an example of a suitable operating environment 150 for incorporation into the biopsy needle visualization system 100. In its most basic configuration, operating environment 150 typically includes at least one processing unit 152 and memory 154. Depending on the exact configuration and type of computing device, memory 154 (storing instructions to perform the active monitoring embodiments disclosed herein) may be volatile (such as RAM), non-volatile (such as ROM, flash memory, etc.), or some combination of the two. This most basic configuration is illustrated in FIG. 1E by dashed line 156. Further, environment 150 may also include storage devices (removable 158, and/or non-removable 160) including, but not limited to, magnetic or optical disks or tape. Similarly, environment 150 may also have input device(s) 164 such as keyboard, mouse, pen, voice input, etc. and/or output device(s) 166 such as a display, speakers, printer, etc. The input devices 164 may also include circuitry or interfaces to receive or detect signals emitted from the various components of the biopsy needle visualization system 100, such as the ultrasound probe 102. Also included in the environment may be one or more communication connections 162, such as LAN, WAN, point to point, etc. In embodiments, the connections may be operable to facility point-to-point communications, connection-oriented communications, connectionless communications, etc.

Operating environment 150 typically includes at least some form of computer readable media. Computer readable media can be any available media that can be accessed by processing unit 152 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 150 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media.

Figure 2:
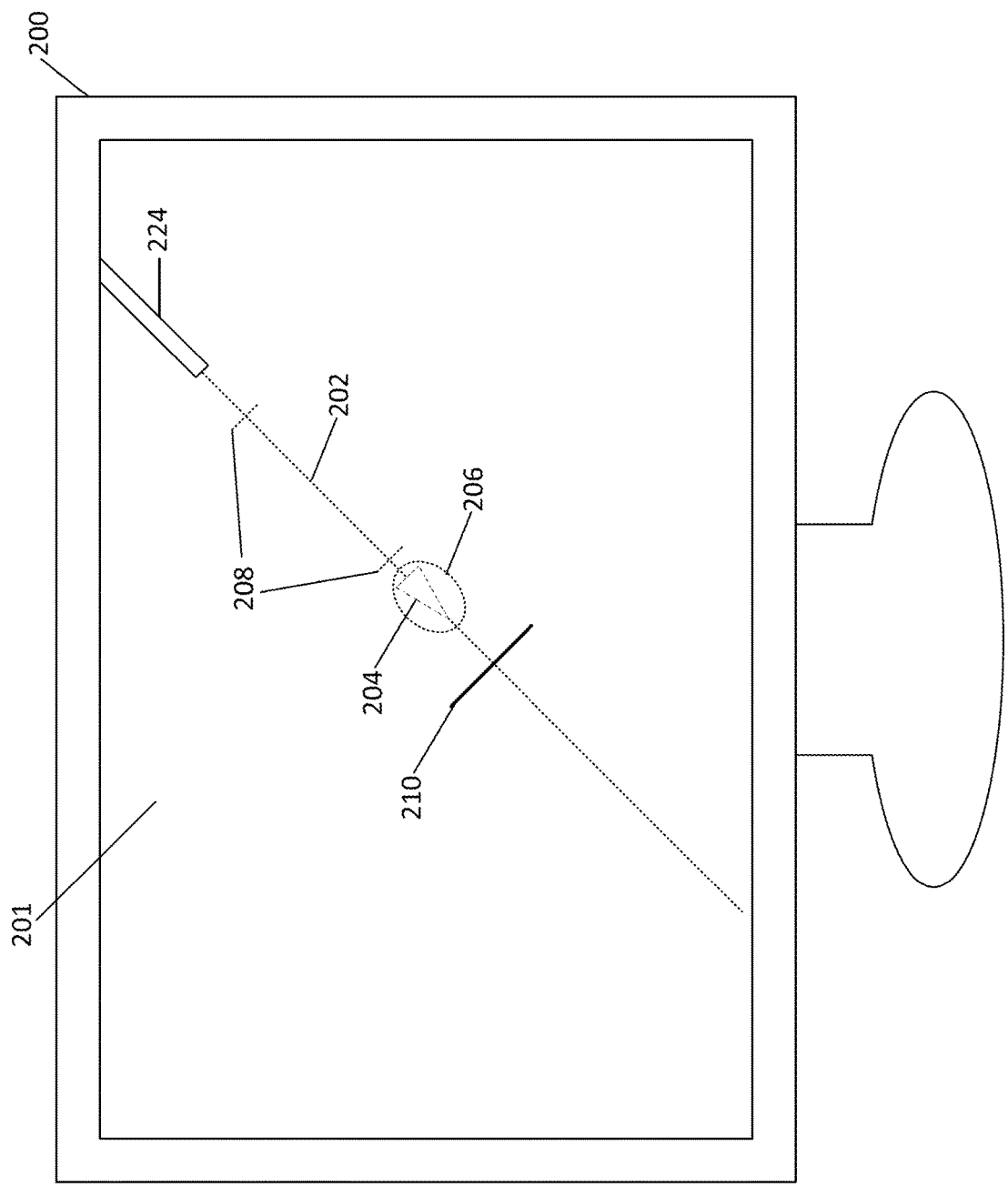
FIG. 2 depicts an example ultrasound image including biopsy needle prediction indicators.

FIG. 2 depicts an example of an ultrasound image 201 including a biopsy needle 224 and multiple biopsy needle prediction indicators. The ultrasound image is displayed on a display 200. The display 200 may be the display 110 discussed above with reference to FIG. 1A. The ultrasound image 201 is an example of an ultrasound image where the biopsy needle 224 is within the field of view of the ultrasound probe. The ultrasound image 201 is generated from image data generated from the detected reflected ultrasonic sound waves. Based on the image data or the ultrasound image 201, the biopsy needle 224 may be identified through the use of image analysis techniques. The shape of the biopsy needle 224 is generally distinguishable from the other tissue or internal portions of the human body. For instance, the biopsy needle 224 has shape that is not naturally occurring in the human body. Further, the material of the biopsy needle 224 may also be manufactured in whole or in part from a material that makes the marker easier to detect within the ultrasound image 201 or image data. For instance, at least a portion of the material of the biopsy needle 224 may be a material that has a high degree of echogenicity, which causes that portion of the biopsy needle 224 to appear brighter in the resulting ultrasound image 201. Air or other gas within the biopsy needle may also cause the biopsy needle 224 to appear brighter in the ultrasound image 201.

Accordingly, based on the distinguishing shape and material of the biopsy needle 224, image analysis techniques may more easily identify the biopsy needle within the ultrasound image 201. The image analysis techniques may also be based on machine learning techniques, such as neural networks, deep learning algorithms, statistical analysis techniques, enhanced contrast techniques, or other pattern recognition or matching techniques that are trained based on the shape of the biopsy needle. As an example, the image analysis algorithms may first be trained on a set of ultrasound images containing a particular type of biopsy needle 224. The current ultrasound image 201 or image data is then provided as an input into the trained image analysis algorithms to detect or identify the biopsy needle 224. Identifying the biopsy needle 224 may be based on the cross-section of the biopsy needle 224 as the ultrasound image 201 is a two-dimensional image with a cross-section of the biopsy needle 224.

In additional examples, an ultrasound technician, surgeon, or other user may provide additional input to assist in the identification of the biopsy needle 224 in the ultrasound image 201. For example, input may be provided indicating the type of biopsy needle that is being used for the biopsy procedure. In an example, the input may include providing a model number, make, or other identifying information for the biopsy needle 224. Based on the input from the user, the system may obtain the dimensions and other information about the biopsy needle 224, such as from a local or remote database storing such information. The local or remote database may be preprogrammed with several biopsy needle models, makes or types and include the associated geometries associated with the biopsy needles. The dimensions of the biopsy needle 224 may then be used by the image analysis techniques to assist in identification of the biopsy needle 224 within the ultrasound image 201. The additional input from the ultrasound technician, surgeon, or other user may also include directly identifying the biopsy needle on the ultrasound image 201, such as receiving pointer, touch, or other input to locate the biopsy needle 224. For instance, the ultrasound technician may select the biopsy needle 224 by clicking on the biopsy needle 224 with a mouse on a display of the ultrasound image. The input identifying the biopsy needle 224 (such as click on the image of the biopsy needle 224) may also be utilized in the image analysis techniques to limit the area of the ultrasound image 201 to be analyzed. For example, upon receiving a selection of the biopsy needle 224 from an ultrasound technician, a predetermined area around the selection point may be analyzed to identify the biopsy needle 224. In other examples, two-dimensional input (such as box) may be provided by the ultrasound technician to provide a boundary for an area that is to be analyzed by the image analysis techniques to identify the biopsy needle 224. In other examples, a combination of both user input on the display of the ultrasound image and image analysis techniques may be used to determine the biopsy needle 224.

Once the biopsy needle 224 is identified in the ultrasound image 201, biopsy needle prediction indicators may be generated based on the predicted location of the biopsy needle 224 after firing. The biopsy needle prediction indicators indicate the predicted location of the biopsy needle 224 and the elements thereof after firing of the biopsy needle 224. For example, when the biopsy needle 224 is fired, the biopsy needle 224 may deflect before coming to rest in its post-fire configuration state. The deflections of the biopsy needle 224 is based in part on the properties of the biopsy needle 224 along with the characteristics or properties of the tissue through which the biopsy needle 224 passes during firing. The predicted locations of the elements of the biopsy needle 224 represented by the biopsy needle prediction indicators are determined in light of the biopsy needle 224 properties and/or the tissue characteristics, as discussed further below.

For example, breast tissue comprises glandular, connective, and fat tissue. Patients undergoing breast biopsy may have differing relative amount of these different types of breast tissue. For example, dense breasts have relatively high amounts of glandular tissue and fibrous connective tissue and relatively low amounts of fatty breast tissue. On the other side of the spectrum, a breast may be predominately made of fatty breast tissue. Other characteristics of breast tissue may include scattered areas of dense glandular tissue and fibrous connective tissue and heterogeneously dense breast tissue with many areas of glandular tissue and fibrous connective tissue. Different characteristics of breast tissue may result in different locations for the prediction indicators for the biopsy needle 224. In one example, breast tissue having higher degrees of density or stiffness may result in more deflection of the biopsy needle 224 when the biopsy needle 224 passes through the breast tissue during firing. The characteristics of the breast tissue may be determined through image analysis and/or input from a user indicating the characteristics of the breast tissue. Portions of breast tissue may be highlighted or otherwise emphasized in the ultrasound image. For instance, if a particularly dense or stiff portion of tissue is identified through image analysis and/or user input, that portion of tissue may be highlighted or otherwise emphasized on the ultrasound image to alert the medical professional to the existence of the tissue.

The biopsy needle prediction indicators include a trajectory indicator 202, a tip indicator 204, a deflection probability indicator 206, aperture indicators 208, and a maximum needle depth indicator 210. The trajectory indicator 202 indicates the trajectory of the biopsy needle 224. For instance, if the biopsy needle 224 was fired in its current position in the ultrasound image 201, the throw portion of the biopsy needle 224 is predicted to follow the line of the trajectory indicator 202. As depicted in FIG. 2, the trajectory indicator 202 may be displayed as line extending from the biopsy needle 224 and extending substantially parallel to the biopsy needle 224. The tip indicator 204 indicates the most likely position of the tip of the biopsy needle 224 in its post-fire configuration. For example, if the biopsy needle 224 were fired from its current position in the current ultrasound image 201, the most likely location for the tip of the biopsy needle 224 in the post-fire configuration is shown by the tip indicator 204. The biopsy needle 224 may be in the shape of a triangle or have a shape that more closely resembles a tip shape of a current biopsy needle 224 being used for the procedure. For instance, the shape of the tip indicator 204 may be based on the geometry of the tip of the biopsy needle 224 being used for the biopsy. Accordingly, the shape of the tip indicator 204 may change based on the particular biopsy needle 224 being used to perform the biopsy. Other shapes for the tip indicator 204 are also possible, including lancet tip needle, trocar tip needle, bevel tips, and multiple point tips, among others. A deflection probability indicator 206 is also displayed adjacent to the tip indicator 204. The deflection probability indicator 206 indicates a range for a predicted post-fire tip location based on a determined deflection probability for the biopsy needle 224. For example, the tip indicator 204 may indicate the most likely predicted position for the tip of the biopsy needle 224, and the deflection probability indicator 206 may encompass all possible predicted locations for the tip of the biopsy needle 224. In other examples, the deflection probability indicator 206 may encompass a significant portion of the possible predicted tip locations, such as 80% likelihood or the predicted tip locations within one or two standard deviations from the most likely tip location. The deflection probability indicator 206 may be in the shape of an ellipse, a circle, square, rectangle, or other shape. The deflection probability indicator 206 may also be in the form of a heatmap showing the probability distribution for the predicted tip location.

The aperture indicators 208 indicate the predicted location for the aperture of the biopsy needle 224 in its post-fire configuration. By seeing the predicted location for the aperture represented by the aperture indicators 208, a surgeon is able to more accurately predict if the aperture will be in the targeted location (e.g., a lesion or mass) after the biopsy needle 224 is fired. The aperture indicators 208 may be represented by two line segments that are perpendicular to the trajectory indicator 202. The distance between the aperture indicators 208 represents the length of the aperture of the particular biopsy needle 224 that is being used to perform the biopsy. Accordingly, the distance between the aperture indicators 208 may change for different biopsy needles.

The maximum needle depth indicator 210 indicates a maximum depth the biopsy needle 224 may extend in its pre-fire configuration where a prediction for the tip location may still be made. For instance, if the biopsy needle 224 in its pre-fired configuration were to pass the maximum needle depth indicator 210, the tip of the biopsy needle 224 would be outside the current ultrasound image 201. The maximum needle depth indicator 210 may be a line segment that is perpendicular to the trajectory indicator 202. While the biopsy needle prediction indicators have been described and depicted as having certain shapes or orientations, other shapes and orientations are also contemplated herein. For instance, while some of the indicators are displayed in dashed lines and others in solid lines, the technology is not limited to such examples.

Figure 3A:
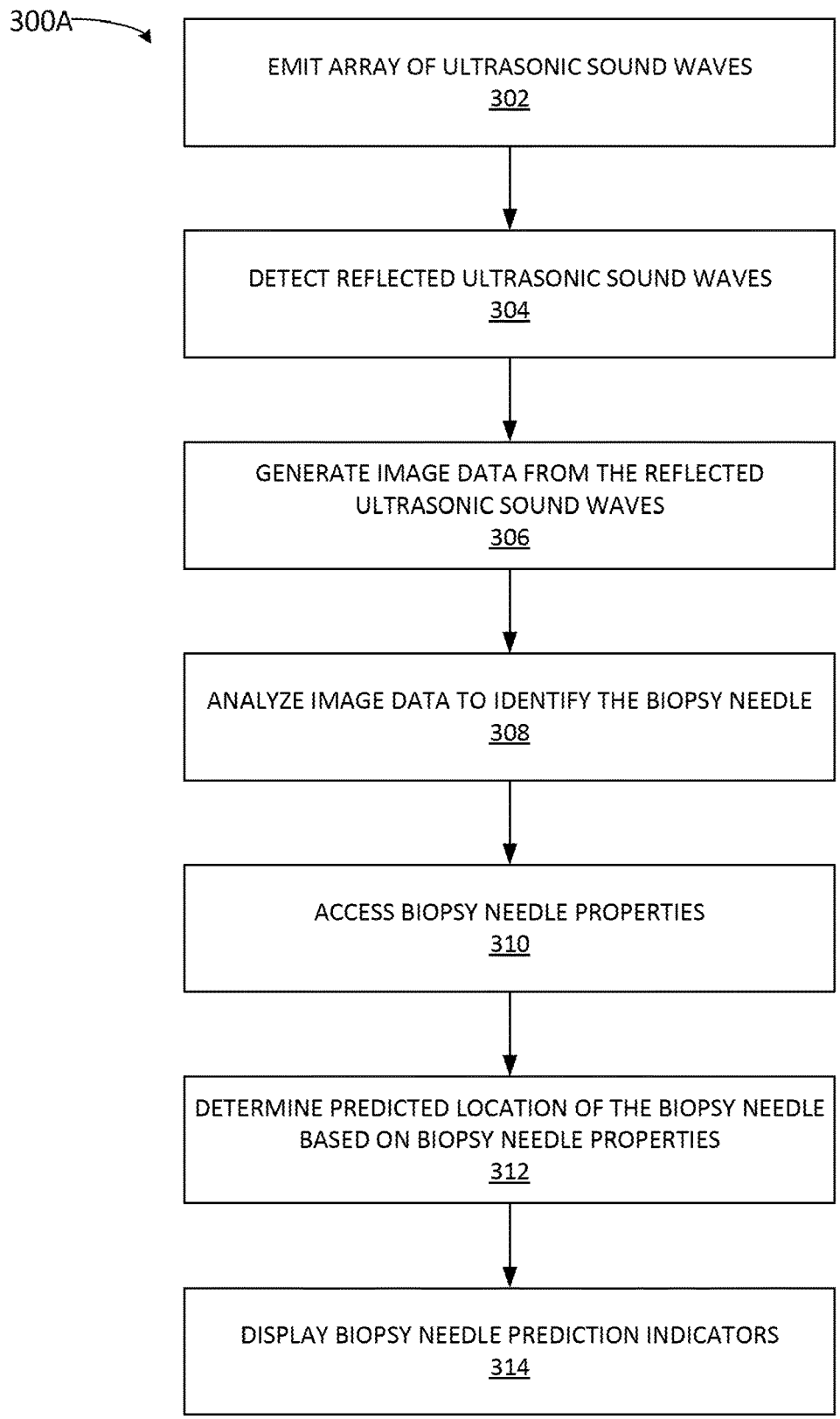
FIG. 3A depicts an example method for visualization of a biopsy needle.

FIG. 3A depicts an example method 300A for predictive visualization of a biopsy needle. The predictive visualization method 300A provides for additional guidance and biopsy needle prediction indicators to be displayed on ultrasound as a biopsy is being performed. As such, a surgeon performing the biopsy is able to receive substantially real-time guidance for performing the biopsy. The operations of method 300A and the other methods discussed herein may be performed by at least one processor in conjunction with other components of a suitable operating environment, such as the operating environment 150 in FIG. 1G, within a system such as system 100 depicted in FIGS. 1A-1C.

At operation 302, an array of ultrasonic sound waves are emitted from an ultrasonic transducer of an ultrasound probe. The ultrasound waves enter the interior of the patient and are reflected from the components of the interior of the patient, including natural tissue as well as the biopsy needle, as discussed above. The reflected ultrasonic waves are then detected at operation 304. At operation 306, ultrasound image data is then generated from the detected reflected ultrasonic sound waves. The ultrasound image data may be B-mode ultrasound imaging data.

At operation 308, the image data is analyzed by a processor of the biopsy needle visualization system to identify or detect the biopsy needle within the image data. As discussed above, the image analysis techniques may be based on image processing techniques, and machine learning techniques, such as neural networks, deep learning algorithms, or other pattern matching techniques, that are trained based on the shape of the marker implanted in the patient. As an example, the image analysis algorithms may first be trained on a set of ultrasound images containing the biopsy needle in different orientations and views. A current ultrasound image or image data is then provided as an input into the trained image analysis algorithms to detect or identify the biopsy needle. Identifying the marker may generally be based on the shape and dimensions of the biopsy needle.

At operation 310, properties for the biopsy needle are accessed or otherwise determined. The properties for the biopsy needle at least one of a needle length, a needle gauge, a needle wall thickness, a needle material composition, a needle tip geometry, and a needle firing mechanism property, aperture length, throw length, among other potential biopsy needle properties. The properties for the biopsy needle may be accessed by querying a database stored locally in the biopsy needle visualization system 100 or a remote database accessible from the biopsy needle visualization system 100. In an example, a user interface may first be displayed at the beginning of a biopsy procedure to allow for a selection or input a type of biopsy needle to be used in the biopsy procedure. In an example, the input into the user interface may indicate a particular make or model of the biopsy needle. In such an example, the input into the user interface may be used to query the respective database to access or determine the properties for the biopsy needle indicated by the input into the user interface. In other examples, the properties of the biopsy needle (e.g., needle length, gauge, etc.) are provided directly as input into the user interface. In such an example, no database query is performed as the properties have already been provided directly.

At operation 312, the predicted location of the biopsy needle is determined. Determining the predicted location of the biopsy needle may be include determining the location of the aspects or portions of the biopsy needle, such as the needle tip, the aperture, the throw portion, or other features of the biopsy needle. For example, the location of the biopsy needle in a post-fire configuration may be determined. In such an example, the various aspects of the biopsy needle, such as the needle tip, aperture, throw portion, and/or other features, aspects, or portions of the biopsy needle, may be determined for needle in the post-fire configuration. The determination of the predicted location of the biopsy needle may be based on the biopsy needle properties accessed or determined in operation 310. In addition, the determined predicted location for the biopsy needle may be based on tissue properties as well. At operation 314, biopsy needle prediction indicators are displayed on an ultrasound image. For example, the biopsy needle prediction indicators may include one or more of a trajectory indicator, a tip indicator, a deflection probability indicator, aperture indicators, and a maximum needle depth indicator. Displaying the prediction indicators may also include changing the state of the prediction indicators. For instance, as the biopsy needle in its pre-fire position is moved within the patient, the state of the prediction indicators may change. As an example, the displayed location of the prediction indicators may change as the biopsy needle is repositioned. The prediction indicators may also include audible indicators or tactile indicators in the biopsy device. Additional details regarding the determination of the predicted location of the biopsy needle are discussed below with reference to FIGS. 3B and 3C.

In addition to the prediction indicators, additional positioning indicators may be displayed indicating to the medical professional how to alter the position of the biopsy needle to more accurately target the lesion or area of interest. For instance, the lesion or area of interest may be identified through image analysis and/or user input. If the predicted location of the biopsy needle aperture is not aligned with the lesion, positioning indicators may be displayed to guide the medical professional on how to move the needle into a position where the predicted location of the needle aperture more accurately targets the lesion. Such positioning indicators may be in the form of arrows and/or text, among other indicators, that provide the positioning guidance. In addition, visual, tactile, and/or audible positioning indicators may be displayed that indicate proper positioning of the biopsy needle. As an example, when the needle is positioned such that the aperture of the needle will properly target the lesion, tactile, audible, and/or visual feedback may be provided. For instance, an audible sound may be provided, and the sound may change volume or frequency as the biopsy needle is moved toward or away from properly targeting the lesion or area of interest.

Figure 3B:
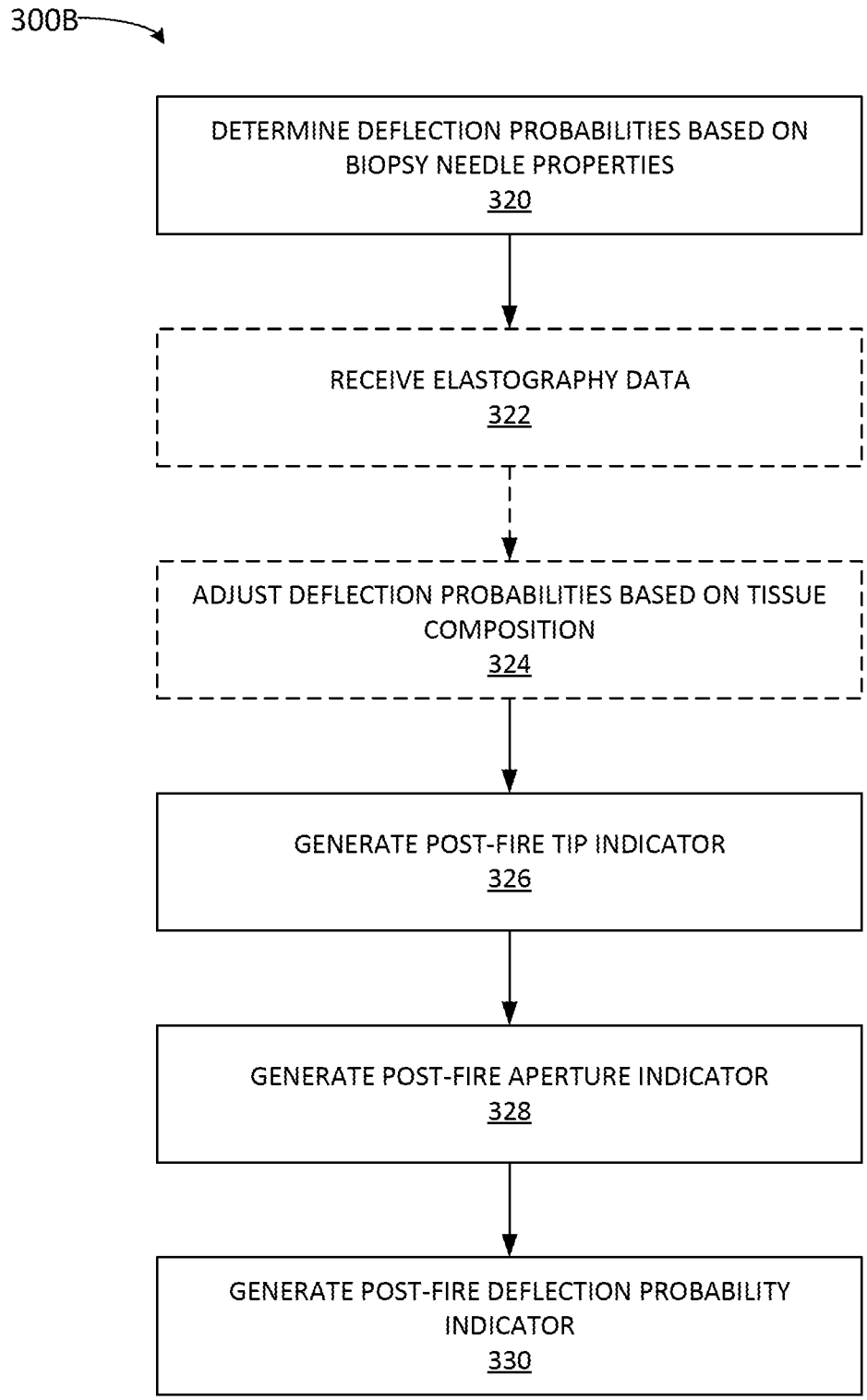
FIG. 3B depicts another example method for visualization of a biopsy needle.

FIG. 3B depicts another example method 300B for predictive visualization of a biopsy needle. At operation 320, deflection probabilities for the particular biopsy needle being used in the biopsy procedure are determined based on the properties for the particular biopsy needle. When a biopsy needle is fired, the throw portion may deflect due to the internal tissue of the patient. The direction and amount of deflection is based on the biopsy needle properties as well as the type of tissue that the biopsy needle passes through when fired. As discussed above, the biopsy needle properties may include one or more of a needle length, a needle gauge, a needle wall thickness, a needle material composition, a needle tip geometry, and a needle firing mechanism property, aperture length, throw length, among other potential biopsy needle properties. Each of these properties may have an effect on the deflection of the biopsy needle when fired. For example, a biopsy needle with a long length, but a large gauge (i.e., small diameter) may be more likely to deflect when fired. Similarly, needles with thinner wall thicknesses may also be more likely to have a greater degree of deflection. The geometry of the tip of the biopsy needle also affects the amount of deflection as well as the direction of deflection. The firing mechanism properties of the biopsy needle further affect the deflection due to the force with which the needle is fired. The other properties of the biopsy needle may also have effects on the magnitude and/or direction of the deflection of the biopsy needle.

The deflection probabilities of the biopsy needle may be determined analytically and/or be based on a set of experimental data. For instance, based on the properties of the needle, a mathematical prediction may be made as to the probability of the final needle position and its deflection. The mathematical prediction may be based on the mechanical behavior of a hollow cylinder advancing through a material having a density and/or stiffness similar to that of human tissue at the biopsy site. The properties of the hollow cylinder or tube may be modified based on the properties of the biopsy needle and the resultant flex of the hollow cylinder or tube. Computerized simulations for the biopsy needle may also be processed to determine the probabilities of the biopsy needle deflection. The results of the computerized simulations provide the deflection probabilities for the biopsy needle. The deflection probabilities may also be determined empirically a set of experimental results. For example, a biopsy needle may be inserted into a replica of a breast (or other human tissue particular to the biopsy site) and fired. The deflection of the needle may be tracked using the biopsy needle visualization system. The testing may be repeated form an experimental data set for different biopsy needles. For example, experimental data may be generated for a needle passing through dense tissue and for a needle passing through adipose tissue. The deflection properties for a particular biopsy needle may be determined from the experimental data set.

At operation 322, elastography data is optionally received. The elastography data may be elastography data for the tissue along the fire trajectory for the biopsy needle (e.g., the path along which the biopsy needle will pass when fired). The elastography data may be obtained directly from the biopsy needle visualization system. As an example, the imaging mode of the ultrasound components may be include an elastography mode that provides elastography data indicated the stiffness or other elastic properties of the tissue. The elastography data may be received from other sources as well based on known tissues at the biopsy site. In one example, a fire trajectory may be determined in part based on ultrasound image data, and the fire trajectory may have already been determined for the trajectory indicator. Elastography data is then received for at least a portion of the tissue along the fire trajectory. Based on the elastography data received, tissue properties may be determined for the tissue along the fire trajectory.

At operation 324, tissue properties of the patient may be used to adjust the deflection probabilities. The tissue characteristics may be tissue characteristics along the fire trajectory for the needle or general tissue characteristics for the biopsy site. In some examples, the tissue characteristics are determined for a predetermined distance around the fire trajectory. The tissue properties may be determined from the elastography data received or captured in operation 322, image analysis of an ultrasound image, and/or user input. For example, where the elastography data indicates that there is a stiff portion of tissue within the biopsy needle fire trajectory, deflection may be more likely to occur. The deflection probabilities may then be updated based on the stiffness of the portion of the tissue and/or the location of the portion of the tissue. Other tissue properties, such as density and/or tissue composition, may also be incorporated to adjust the deflection probabilities. In an example, such tissue properties may be identified through image analysis of the ultrasound image. For example, tissue characteristics may be determined for a portion of tissue appears brighter in the ultrasound image and/or has a particular shape. In addition, a user may also provide input that identifies a portion of tissue and provides tissue characteristics (such as density, stiffness, etc.) for the identified tissue. The user input and/or image analysis may also identify the type of tissue in the ultrasound image. For example, the user input and/or image analysis may identify portions of tissue as either glandular tissue, connective tissue, or fat tissue. The tissue characteristics for the type of tissue may then be accessed or received, such as from a local or remote database, and those tissue characteristics may then be used in determining the deflection probabilities. The tissue properties may also be incorporated directly into the probability deflection determination in operation 320.

At operation 326, a tip indicator is generated based on the deflection probabilities and the properties for the biopsy needle. The tip indicator may be for the biopsy needle in its post-fire configuration. For example, based on the length of the throw portion for the particular needle and the deflection probabilities, the predicted location for the tip of the biopsy needle in the post-fire configuration may be determined, and the tip indicator may be generated based on that determination. At operation 328, an aperture indicator (or aperture indicators) may be generated based on the deflection probabilities and the properties for the biopsy needle. The aperture indicator may be for the biopsy needle in its post-fire configuration. For example, based on the length of the throw portion, the aperture location, and the deflection probabilities, a predicted location for the aperture of the biopsy needle in the post-fire configuration may be determined. The aperture indicator may be generated based on that determination. At operation 330, a deflection probability indicator is generated. The deflection probability indicator may be for the tip of the biopsy needle in its post-fire configuration. The deflection probability indicator is based on the determined deflection probabilities. The deflection probability indicator indicates a range for a predicted post-fire tip location based on a determined deflection probability for the biopsy needle. For example, the tip indicator may indicate the most likely predicted position for the tip of the biopsy needle, and the deflection probability indicator may encompass all possible predicted locations for the tip of the biopsy needle. In other examples, the deflection probability indicator may encompass a significant portion of the possible predicted tip locations, such as 90%, 80%, or 70% likelihood or the predicted tip locations within one or two standard deviations from the most likely tip location. To show the probability distribution for the determined deflection probabilities, the deflection probability indicator may also be in the form of a heatmap.

Figure 3C:
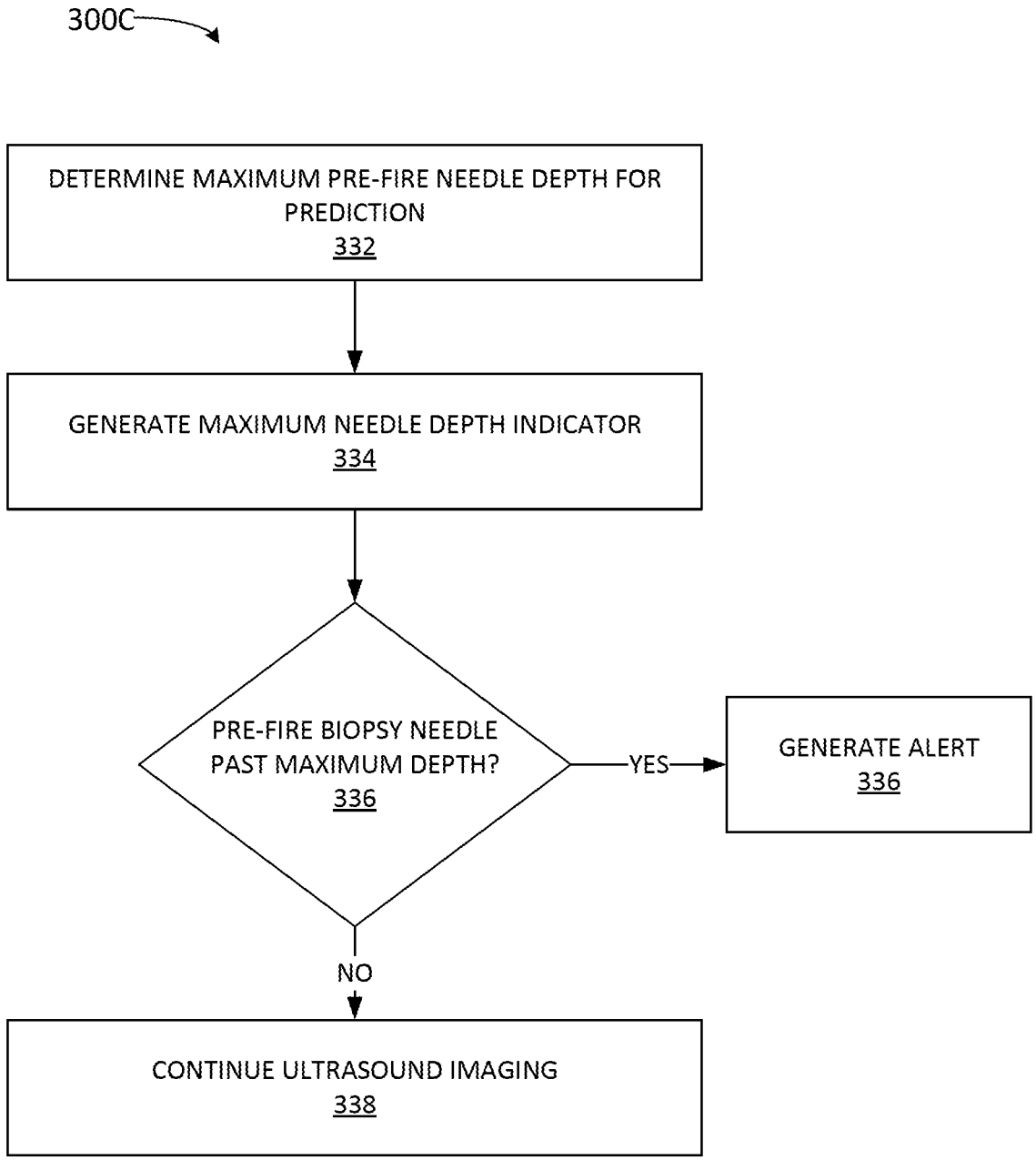
FIG. 3C depicts another example method for visualization of a biopsy needle.

FIG. 3C depicts another method 300C for predictive visualization of a biopsy needle. At operation 332, a maximum pre-fire biopsy needle depth for prediction is determined. The maximum pre-fire biopsy needle depth is a maximum depth the biopsy needle may extend in its pre-fire configuration where a prediction for the tip location may still be made. The determination of the maximum pre-fire biopsy needle depth may be based on the predicted tip location and the size of the display displaying the ultrasound image. Based on the determined maximum pre-fire biopsy needle depth, a maximum needle depth indicator is generated and may be displayed in the position of the determined maximum pre-fire biopsy needle depth.

At operation 336, a determination is made as to whether the biopsy needle in its pre-fire configuration has passed the maximum pre-fire biopsy needle depth. If the biopsy needle has passed the maximum pre-fire biopsy needle depth, the method 300C flows to operation 336 where an alert is generated that alerts the surgeon a tip location predication can no longer be presented on the screen. The alert may be visual, audible, or tactile. In an example, an audible or tactile indicator may be also provided that changes frequency or amplitude as the biopsy needle approaches the maximum pre-fire biopsy needle depth. Accordingly, based on the changing state of the indicator, the medical professional may be provided continuous guidance as to the positioning of the biopsy needle. If the biopsy needle depth has not passed the maximum pre-fire biopsy needle depth, ultrasound imaging continues and the maximum pre-fire biopsy needle depth indicator remains displayed for visual reference for the surgeon.

Figure 4:
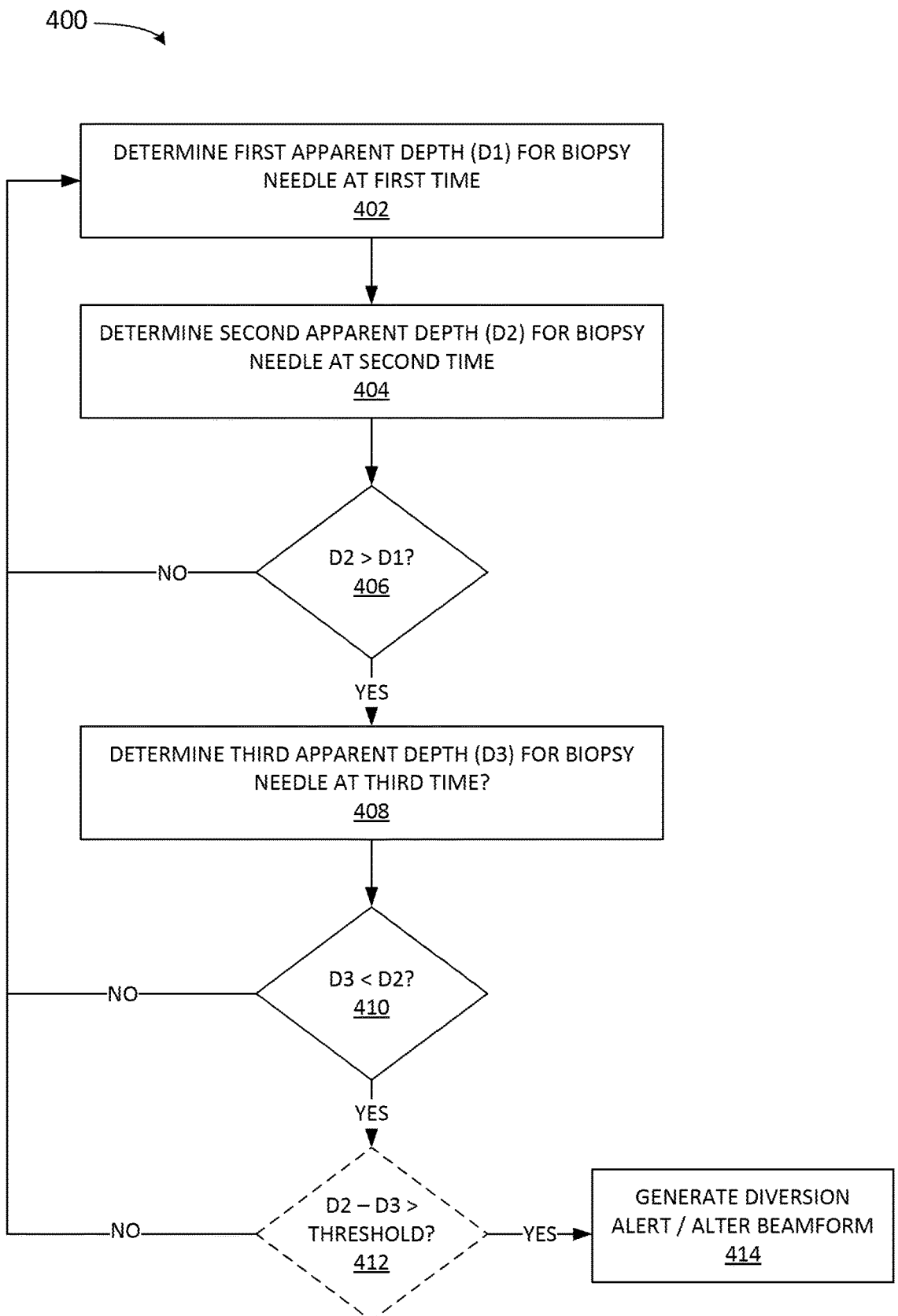
FIG. 4 depicts an example method for detecting plane diversion of a biopsy needle.

FIG. 4 depicts an example method 400 for detecting plane diversion of a biopsy needle. In an ultrasound image, the biopsy needle can be seen to advance to further depths into the patient when the biopsy needle is substantially aligned with the imaging plane of the ultrasound imaging system. If the needle diverts out of the imaging plane, the needle appears in the ultrasound image to no longer be advancing, despite the needle actually moving further into the patient. In some instances, a reduction in the apparent depth of the needle may be seen in the ultrasound image. If the reduction in apparent depth does not correspond with the needle being retracted from the patient, it is likely that the surgeon has diverted the needle out of the imaging plane and may need to readjust either the needle or the ultrasound imaging probe. Method 400 provides an alert or a change in beamform from the ultrasound imaging probe as a result to such a diversion of the needle out of the imaging plane.

At operation 402, a first apparent depth (D1) for the biopsy needle is determined at a first time (t1). The apparent depth of the biopsy needle is the depth of the biopsy needle into the patient as it appears in the ultrasound image. In some examples, the apparent depth of the needle may be determined by measuring the length of the portion of the biopsy needle that appears in the ultrasound image. At operation 404, the apparent depth of the needle is determined again at a subsequent time (t2). This subsequent apparent depth is a second apparent depth (D2). At operation 406, a determination is made as to whether D2 is greater than D1. If D2 is not greater than D1, the needle may not be advancing or may be being retracted. As such, the method 400 returns to operation 402 where the method 400 repeats. If D2 is greater than D1, the needle is likely advancing into the patient on the imaging plane, and the method 400 flows to operation 408. At operation 408, a third apparent depth (D3) is measured at a time (t3) subsequent to the time (t2). At operation 410 a determination is made as to whether D3 is less than D2. If D3 is greater than D2, the needle is still advancing and in the imaging plane, and method 400 returns to operation 402 where method 400 repeats. If D3 is less than D2, either the needle has diverted out of the imaging plane or has been retracted. If D3 is less than D2, method 400 flows to optional operation 412, where the difference between D3 and D2 are compared to determine if the difference exceeds a threshold value. By comparing the difference between D3 and D2 to a threshold, false alarms may be avoided where only minor shifts in apparent depth are observed. If the different between D2 and D3 is less than the threshold, the method 400 flows back to operation 402 where method 400 repeats. If the difference between D2 and D3 exceeds the threshold, the method 400 flows to operation 414 where a diversion alert may be generated. The diversion alert indicates that the needle may have diverted out of the imaging plane for the ultrasound image. The diversion alert allows the surgeon to reposition the needle or the ultrasound probe to bring the needle back in line with the imaging plane. The surgeon may also ignore or silence the alert if the needle is actually being retracted from the patient. In addition, positioning indicators may be displayed indicating to the medical professional how to alter the position of the biopsy needle to bring the biopsy needle back into the imaging plane. For instance, if the needle has diverted out of the imaging plane, a positioning indicator may be displayed in operation 414. The positioning indicator may be in the form of arrows and/or text, among other possible indicators, that provide guidance to the medical professional as to how the needle should be moved to bring the needle back into the imaging plane.

At operation 414, the beamform of ultrasound waves emitted from the ultrasound probe may also be altered to alter the imaging plane. For instance, by altering the beamform of the ultrasound waves, the direction of the waves may be altered to modify the resultant imaging plane. When a potential diversion is detection (such as D3 being less than D2), the beamform may be altered. The alteration of the beamform may be predetermined based on the movement of the needle, or the beamform may change until an apparent depth for the needle can be determined that is greater than D2.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method for providing guidance for operation of a biopsy needle, the method comprising:
    emitting an array of ultrasonic sound waves from an ultrasonic transducer of an ultrasound probe;
    detecting reflected ultrasonic sound waves by the ultrasonic transducer, wherein the reflected ultrasonic sound waves include at least a portion of the array of ultrasonic sound waves after being reflected from an interior of a patient;
    generating image data from the reflected ultrasonic sound waves;
    identifying, by a processor, within the generated image data, at least a portion of the biopsy needle within the interior of the patient;
    based at least in part on the identification the portion of the biopsy needle, determining, by the processor, a predicted location of an aspect of the biopsy needle based at least in part on one or more biopsy needle properties stored in memory operatively connected to the processor, the biopsy needle properties comprising at least one of a needle length, a needle gauge, a needle wall thickness, a needle material composition, a needle tip geometry, and a needle firing mechanism; and
    displaying, on a display operatively connected to the processor, an ultrasound image based on the generated image data;
    determining a deflection probability for a post-fire needle tip location based on at least one of: (1) experimental data for the type of biopsy needle and (2) the one or more stored properties of the biopsy needle; and
    displaying a deflection probability indicator on the ultrasound image, wherein the deflection probability indicator indicates a range for the post-fire needle tip locations based on the determined deflection probability, wherein the deflection probability indicator depicts a probability distribution for the post-fire needle tip location;
    wherein the deflection probability indicator is based at least in part on a standard deviation of the post-fire needle tip locations.

2. The method of claim 1, wherein identifying the biopsy needle includes identifying the biopsy needle in a pre-fire configuration, and the predicted location of the biopsy needle is a predicted location of the biopsy needle in a post-fire configuration.

3. The method of claim 1, further comprising displaying at least one indicator for the predicted location of the biopsy needle that includes displaying at least one of a tip indicator indicating a predicted biopsy needle tip location or an aperture indicator indicating a predicted biopsy needle aperture location.

4. The method of claim 1, wherein identifying the biopsy needle comprises receiving a user input identifying the biopsy needle in the ultrasound image.

5. The method of claim 1, wherein identifying the biopsy needle comprises analyzing, by the processor, the generated image data by image analysis techniques to identify the biopsy needle.

6. The method of claim 1, wherein determining the deflection probability is further based on tissue properties of the interior of the patient along a fire trajectory for the biopsy needle.

7. The method of claim 6, wherein the tissue properties are based on an input identifying the tissue properties.

8. The method of claim 6, further comprising determining the tissue properties by:
    determining, by the processor, a fire trajectory for the biopsy needle based on the generated image data;
    receiving elastography data for tissue along at least a portion of the fire trajectory for the biopsy needle; and
    determining the tissue properties based on the received elastography data.

9. The method of claim 1, further comprising:
    determining that the biopsy needle has diverted out of an imaging plane of the ultrasound image; and
    in response to determining that the biopsy needle has diverted out of the imaging plane for the ultrasound image, performing at least one of the following operations:
        displaying an alert indicating that the biopsy needle has diverted out of the imaging plane for the ultrasound image; or
        altering a beamform emitted from the ultrasound probe to compensate for the biopsy needle diversion out of the imaging plane.

10. The method of claim 9, wherein determining that the biopsy needle has diverted out of the imaging plane for the ultrasound image further comprises:
    determining a first apparent depth for the biopsy needle at a first time;
    determining a second apparent depth for the biopsy needle at a second time subsequent to the first time, the second apparent depth being greater than the first apparent depth;
    determining a third apparent depth for the biopsy needle at a third time subsequent to the second time, the third apparent depth being less than the second apparent depth; and
    based on the third apparent depth being less than the second apparent depth and the second apparent depth being greater than the first apparent depth, determining that the biopsy needle has diverted out of the imaging plane for the ultrasound image.

11. The method of claim 1, wherein the method further comprises obtaining the experimental data for the type of biopsy needle.

12. The method of claim 11, wherein obtaining the experimental data comprises one of:
    passing a needle through dense tissue and passing a needle through adipose tissue; and
    inserting the biopsy needle in a replica of a breast.

13. The method of claim 1, wherein the deflection probability indicator depicts a likelihood of the post-fire needle tip locations.

14. The method of claim 1, wherein the deflection probability indicator comprises a heatmap.

15. The method of claim 1, further comprising overlaying the deflection probability indicator on the ultrasound image.

* * * * *